US010004793B2

(12) United States Patent
Aagaard et al.

(10) Patent No.: US 10,004,793 B2
(45) Date of Patent: *Jun. 26, 2018

(54) M.TUBERCULOSIS VACCINES

(71) Applicant: Statens Serum Institut, Cophenhagen S (DE)

(72) Inventors: Claus Aagaard, Cophenhagen S (DK); Ida Rosenkrands, Vaelose (DK); Truc Thi Kim Thanh Hoang, Glostrup (DK); Peter Lawaetz Andersen, Bronshoj (DK)

(73) Assignee: Statens Serum Institut, Copenhagen S (DK)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/306,239

(22) PCT Filed: Apr. 9, 2015

(86) PCT No.: PCT/DK2015/050086
§ 371 (c)(1),
(2) Date: Oct. 24, 2016

(87) PCT Pub. No.: WO2015/161853
PCT Pub. Date: Oct. 29, 2015

(65) Prior Publication Data
US 2017/0043003 A1  Feb. 16, 2017

(30) Foreign Application Priority Data
Apr. 24, 2014  (DK) .............................. 2014 00226

(51) Int. Cl.
*A61K 39/04* (2006.01)
*C07K 14/35* (2006.01)
(Continued)

(52) U.S. Cl.
CPC .............. *A61K 39/04* (2013.01); *A61K 39/39* (2013.01); *C07K 14/35* (2013.01);
(Continued)

(58) Field of Classification Search
CPC .................... A61K 39/04; A61K 39/00; A61K 2039/55555; A61K 38/00; A61K 2039/51;
(Continued)

(56) References Cited

U.S. PATENT DOCUMENTS 9,526,773 B2   12/2016  Aagaard et al.

FOREIGN PATENT DOCUMENTS

| WO | WO 2010/121618 A1 | 10/2010 |
| WO | WO 2012/057904 A1 | 5/2012 |
| WO | WO 2014/063704 A2 | 5/2014 |

OTHER PUBLICATIONS

Aagaard, C. et al., A multistage tuberculosis vaccine that confers efficient protection before and after exposure, Nature Medicine, Jan. 2011, 17(2): 189-195.
(Continued)

Primary Examiner — Jana A Hines
(74) Attorney, Agent, or Firm — Howson & Howson LLP

(57) ABSTRACT

The present invention is directed to a fusion protein, antigen cocktails and immunological compositions such as vaccines against infections caused by virulent mycobacteria, e.g. by *Mycobacterium tuberculosis, Mycobacterium africanum, Mycobacterium bovis, Mycobacterium microti, Mycobacterium canettii, Mycobacterium pinnipedii* or *Mycobacterium mungi*. The fusion protein, antigen cocktails and immunological compositions are based on proteins secreted by the ESAT-6 secretion system 1 (ESX-1) and are among the most immunodominant *M. tuberculosis* (MTB) antigens.

19 Claims, 6 Drawing Sheets

Figure 1:
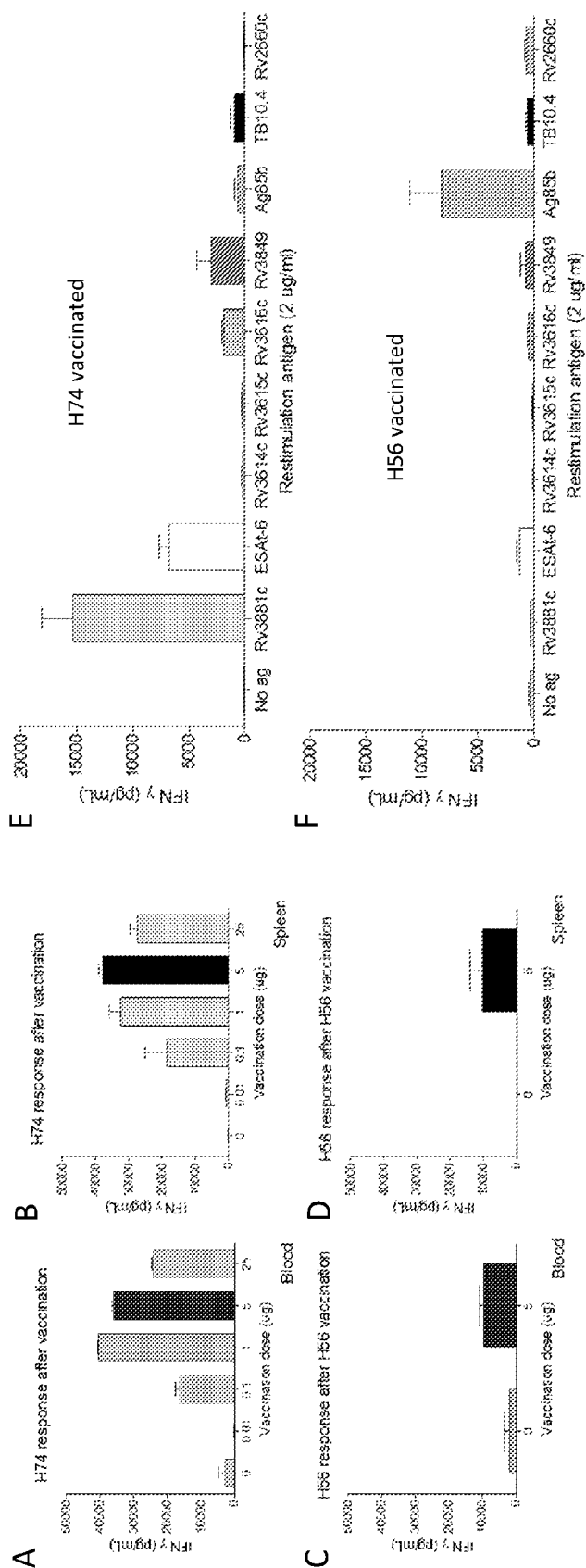

(51) Int. Cl.
A61K 39/39 (2006.01)
A61K 39/00 (2006.01)
(52) U.S. Cl.
CPC ............... A61K 2039/5254 (2013.01); A61K 2039/55555 (2013.01); A61K 2039/575 (2013.01); A61K 2039/70 (2013.01); C07K 2319/00 (2013.01)
(58) Field of Classification Search
CPC .......... A61K 2039/523; A61K 2039/53; A61K 39/39; A61K 2039/545; A61K 2039/55511; A61K 2039/55594; A61K 2300/00; A61K 47/186; A61K 47/26; C07K 14/35; C07K 2319/00; C07K 2319/40
See application file for complete search history.

(56) References Cited

OTHER PUBLICATIONS

Aagaard, C. et al., TB Vaccines: Current Status and Future Perspectives, Immunology and Cell Biology, Apr. 2009, 87(4): 279-286.
Abdallah, M. et al., Type VII secretion—mycobacteria show the way, Perspectives, Nov. 2007, 5: 883-891.
Bahk, Y. et al., Antigens secreted from *Mycobacterium tuberculosis*: Identification by proteomics approach and test for diagnostic marker, Proteomics, Aug. 2004, 4: 3299-3307.
Bold, T.D. et al., Suboptimal Activation of Antigen-Specific CD4+ Effector Cells Enables Persistence of *M. tuberculosis* in Vivo, PLoS Pathogens, May 2011, 7(5): e1002063.
Brodin, P. et al., Dissection of ESAT-6 System 1 of *Mycobacterium tuberculosis* and Impact on Immunogenicity and Virulence, Infection and Immunity, Jan. 2006, 74(1): 88-98.
Champion, P.A.D. et al., C-Terminal Signal Sequence Promotes Virulence Factor Secretion in *Mycobacterium tuberculosis*, Science, Sep. 2006, 313: 1632-1636.
Chen, J.M. et al., EspD Is Critical for the Virulence-Mediating ESX-1 Secretion System in *Mycobacterium tuberculosis*, Journal of Bacteriology, Dec. 2011, 194(4): 884-893.
Cole, S.T. et al., Deciphering the biology of *Mycobacterium tuberculosis* from the complete genome sequence, Nature, Jun. 1998, 393(6685): 537-544.
Das, C. et al., Computational Analysis of the ESX-1 Region of *Mycobacterium tuberculosis*: Insights into the Mechanism of Type VII Secretion System, PLoS One, Nov. 2011, 6(11): e27980.
Egen, J.G. et al., Intravital Imaging Reveals Limited Antigen Presentation and T Cell Effector Function in Mycobacterial Granulomas, Immunity, May 2011, 34(5): 807-819.
Fortune, S.M. et al., Mutually dependent secretion of proteins required for mycobacterial virulence, PNAS, Jun. 2005, 102(30): 10676-10681.
Gao, L.Y. et al., A mycobacterial virulence gene cluster extending RD1 is required for cytolysis, bacterial spreading and ESAT-6 secretion, Molecular Microbiology, Sep. 2004, 53(6): 1677-1693.
Gordon, S.V. et al., Identification of variable regions in the genomes of tubercle bacilli using bacterial artificial chromosome arrays, Molecular Microbiology, May 1999, 32(3): 643-655.
MacGurn, J.A. et al., A non-RD1 gene cluster is required for Snm secretion in *Mycobacterium tuberculosis*, Molecular Microbiology, Sep. 2005, 57(6):1653-1663.
MacGurn, J.A. et al., A Genetic Screen for *Mycobacterium tuberculosis* Mutants Defective for Phagosome Maturation Arrest Identifies Components of the ESX-1 Secretion System, Infection and Immunity, Jun. 2007, 75(6): 2668-2678.
Ohol, Y.M. et al., *Mycobacterium tuberculosis* MycP1 Protease Plays a Dual Role in Regulation of ESX-1 Secretion and Virulence, Cell Host and Microbe, Mar. 2010, 7(3): 210-220.
Pym, A.S. et al., Recombinant BCG Exporting ESAT-6 Confers Enhanced Protection Against Tuberculosis, Apr. 2003, Nature Medicine, 9(5): 533-539.
Raghavan, S. et al., Secreted transcription factor controls *Mycobacterium tuberculosis* virulence, Nature, Aug. 2008, 454(7205): 717-721.
Stanley, S.A. et al., Acute infection and macrophage subversion by *Mycobacterium tuberculosis* require a specialized secretion system, PNAS, Oct. 2003, 100(22): 13001-13006.
International Search Report dated Jul. 23, 2015 in PCT/DK2015/050086 (international stage of present application).
Written Opinion dated Jul. 23, 2015 in PCT/DK2015/050086 (international stage of present application).
Office Action dated May 24, 2016 in U.S. Appl. No. 14/437,998.
Response to Office Action filed Aug. 31, 2016 in U.S. Appl. No. 14/437,998.

SEQUENCE LISTING

<160> NUMBER OF SEQ ID NOS: 15

<210> SEQ ID NO 1
<211> LENGTH: 460
<212> TYPE: PRT
<213> ORGANISM: Mycobacterium tuberculosis

<400> SEQUENCE: 1

```
Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
            20                  25                  30

Pro Ile Thr Pro Cys Glu Leu Thr Ala Ala Lys Asn Ala Ala Gln Gln
            35                  40                  45

Leu Val Leu Ser Ala Asp Asn Met Arg Glu Tyr Leu Ala Ala Gly Ala
        50                  55                  60

Lys Glu Arg Gln Arg Leu Ala Thr Ser Leu Arg Asn Ala Ala Lys Ala
65                  70                  75                  80

Tyr Gly Glu Val Asp Glu Glu Ala Ala Thr Ala Leu Asn Asp Gly
                85                  90                  95

Glu Gly Thr Val Gln Ala Glu Ser Ala Gly Ala Val Gly Gly Asp Ser
                100                 105                 110

Ser Ala Glu Leu Thr Asp Thr Pro Arg Val Ala Thr Ala Gly Glu Pro
            115                 120                 125

Asn Phe Met Asp Leu Lys Glu Ala Ala Arg Lys Leu Glu Thr Gly Asp
        130                 135                 140

Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
                180                 185                 190

Gln Trp Ile Leu His Met Ala Lys Leu Ser Ala Ala Met Ala Lys Gln
                195                 200                 205

Ala Gln Tyr Val Ala Gln Leu His Val Trp Ala Arg Arg Glu His Pro
210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
                245                 250                 255

Ser Glu Lys Val Leu Thr Glu Tyr Asn Asn Lys Ala Ala Leu Glu Pro
                260                 265                 270

Val Asn Pro Pro Lys Pro Pro Ala Ile Lys Ile Asp Pro Pro
                275                 280                 285

Pro Pro Gln Glu Gln Gly Leu Ile Pro Gly Phe Leu Met Pro Pro Ser
        290                 295                 300

Asp Gly Ser Gly Val Thr Pro Gly Thr Gly Met Pro Ala Ala Pro Met
305                 310                 315                 320

Val Pro Pro Thr Gly Ser Pro Gly Gly Leu Pro Ala Asp Thr Ala
                325                 330                 335

Ala Gln Leu Thr Ser Ala Gly Arg Glu Ala Ala Leu Ser Gly Asp
                340                 345                 350

Val Ala Val Lys Ala Ala Ser Leu Gly Gly Gly Gly Gly Val
            355                 360                 365

Pro Ser Ala Pro Leu Gly Ser Ala Ile Gly Gly Ala Glu Ser Val Arg
    370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Met Met Pro Met Gly Ala
            405                 410                 415
```

```
Ala His Gln Gly Gln Gly Gly Ala Lys Ser Lys Gly Ser Gln Gln Glu
            420                 425                 430

Asp Glu Ala Leu Tyr Thr Glu Asp Arg Ala Trp Thr Glu Ala Val Ile
            435                 440                 445

Gly Asn Arg Arg Arg Gln Asp Ser Lys Glu Ser Lys
    450                 455                 460

<210> SEQ ID NO 2
<211> LENGTH: 95
<212> TYPE: PRT
<213> ORGANISM: Mycobacterium tuberculosis

<400> SEQUENCE: 2

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 3
<211> LENGTH: 184
<212> TYPE: PRT
<213> ORGANISM: Mycobacterium tuberculosis

<400> SEQUENCE: 3

Met Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
            20                  25                  30

Ile Gly Val Gly Ser Ala Ala Thr Pro Asp Thr Gly Pro Asp Leu Asp
        35                  40                  45

Asn Ala His Gly Gln Ala Glu Thr Asp Thr Glu Gln Glu Ile Ala Leu
    50                  55                  60

Phe Thr Val Thr Asn Pro Pro Arg Thr Val Ser Val Ser Thr Leu Met
65                  70                  75                  80

Asp Gly Arg Ile Asp His Val Glu Leu Ser Ala Arg Val Ala Trp Met
                85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
        115                 120                 125

Ser Gln Gln Val Asp Ala Asp Glu His Arg Val Ala Leu Leu Arg Lys
    130                 135                 140

Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Asp Cys Pro Ala
                165                 170                 175

Pro Asp Asp Glu Ser Asp Pro Trp
            180
```

```
<210> SEQ ID NO 4
<211> LENGTH: 103
<212> TYPE: PRT
<213> ORGANISM: Mycobacterium tuberculosis

<400> SEQUENCE: 4

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
                20                  25                  30

Ala Ala Gly Leu Gly Glu Ser Val Ala Ile Thr His Gly Pro Tyr Cys
            35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100

<210> SEQ ID NO 5
<211> LENGTH: 392
<212> TYPE: PRT
<213> ORGANISM: Mycobacterium tuberculosis

<400> SEQUENCE: 5

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Glu Leu Ala Ala
            35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Gly His Ala
            115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220
```

```
Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
            245                 250                 255

Gly Leu Ser Ala Ser Ser Gly Leu Ala His Ala Asp Ser Leu Ala Ser
                260                 265                 270

Ser Ala Ser Leu Pro Ala Leu Ala Gly Ile Gly Gly Ser Gly Phe
        275                 280                 285

Gly Gly Leu Pro Ser Leu Ala Gln Val His Ala Ala Ser Thr Arg Gln
290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
            325                 330                 335

Gly Gly Pro Val Gly Met Gly Met His Pro Ser Ser Gly Ala Ser
                340                 345                 350

Lys Gly Thr Thr Thr Lys Lys Tyr Ser Glu Gly Ala Ala Ala Gly Thr
            355                 360                 365

Glu Asp Ala Glu Arg Ala Pro Val Glu Ala Asp Ala Gly Gly Gln
370                 375                 380

Lys Val Leu Val Arg Asn Val Val
385                 390

<210> SEQ ID NO 6
<211> LENGTH: 132
<212> TYPE: PRT
<213> ORGANISM: Mycobacterium tuberculosis

<400> SEQUENCE: 6

Met Ser Thr Thr Phe Ala Ala Arg Leu Asn Arg Leu Phe Asp Thr Val
1               5                   10                  15

Tyr Pro Pro Gly Arg Gly Pro His Thr Ser Ala Glu Val Ile Ala Ala
            20                  25                  30

Leu Lys Ala Glu Gly Ile Thr Met Ser Ala Pro Tyr Leu Ser Gln Leu
        35                  40                  45

Arg Ser Gly Asn Arg Thr Asn Pro Ser Gly Ala Thr Met Ala Ala Leu
50                  55                  60

Ala Asn Phe Phe Arg Ile Lys Ala Ala Tyr Phe Thr Asp Asp Glu Tyr
65                  70                  75                  80

Tyr Glu Lys Leu Asp Lys Glu Leu Gln Trp Leu Cys Thr Met Arg Asp
                85                  90                  95

Asp Gly Val Arg Arg Ile Ala Gln Arg Ala His Gly Leu Pro Ser Ala
            100                 105                 110

Ala Gln Gln Lys Val Leu Asp Arg Ile Asp Glu Leu Arg Arg Ala Glu
        115                 120                 125

Gly Ile Asp Ala
    130

<210> SEQ ID NO 7
<211> LENGTH: 1319
<212> TYPE: PRT
<213> ORGANISM: Mycobacterium tuberculosis

<400> SEQUENCE: 7

Met His His His His His Gly Ser Thr Gln Ser Gln Thr Val Thr
1               5                   10                  15
```

-continued

```
Val Asp Gln Gln Glu Ile Leu Asn Arg Ala Asn Glu Val Glu Ala Pro
             20                  25                  30

Met Ala Asp Pro Pro Thr Asp Val Pro Ile Thr Pro Ser Glu Leu Thr
         35                  40                  45

Ala Ala Lys Asn Ala Ala Gln Gln Leu Val Leu Ser Ala Asp Asn Met
 50                  55                  60

Arg Glu Tyr Leu Ala Ala Gly Ala Lys Glu Arg Gln Arg Leu Ala Thr
 65                  70                  75                  80

Ser Leu Arg Asn Ala Ala Lys Ala Tyr Gly Glu Val Asp Glu Glu Ala
                 85                  90                  95

Ala Thr Ala Leu Asp Asn Asp Gly Glu Gly Thr Val Gln Ala Glu Ser
             100                 105                 110

Ala Gly Ala Val Gly Gly Asp Ser Ser Ala Glu Leu Thr Asp Thr Pro
         115                 120                 125

Arg Val Ala Thr Ala Gly Glu Pro Asn Phe Met Asp Leu Lys Glu Ala
130                 135                 140

Ala Arg Lys Leu Glu Thr Gly Asp Gln Gly Ala Ser Leu Ala His Phe
145                 150                 155                 160

Ala Asp Gly Trp Asn Thr Phe Asn Leu Thr Leu Gln Gly Asp Val Lys
                 165                 170                 175

Arg Phe Arg Gly Phe Asp Asn Trp Glu Gly Asp Ala Ala Thr Ala Ser
             180                 185                 190

Glu Ala Ser Leu Asp Gln Gln Arg Gln Trp Ile Leu His Met Ala Lys
         195                 200                 205

Leu Ser Ala Ala Met Ala Lys Gln Ala Gln Tyr Val Ala Gln Leu His
210                 215                 220

Val Trp Ala Arg Arg Glu His Pro Thr Tyr Glu Asp Ile Val Gly Leu
225                 230                 235                 240

Glu Arg Leu Tyr Ala Glu Asn Pro Ser Ala Arg Asp Gln Ile Leu Pro
                 245                 250                 255

Val Tyr Ala Glu Tyr Gln Gln Arg Ser Glu Lys Val Leu Thr Glu Tyr
             260                 265                 270

Asn Asn Lys Ala Ala Leu Glu Pro Val Asn Pro Pro Lys Pro Pro Pro
         275                 280                 285

Ala Ile Lys Ile Asp Pro Pro Pro Pro Gln Glu Gln Gly Leu Ile
290                 295                 300

Pro Gly Phe Leu Met Pro Pro Ser Asp Gly Ser Gly Val Thr Pro Gly
305                 310                 315                 320

Thr Gly Met Pro Ala Ala Pro Met Val Pro Pro Thr Gly Ser Pro Gly
                 325                 330                 335

Gly Gly Leu Pro Ala Asp Thr Ala Ala Gln Leu Thr Ser Ala Gly Arg
             340                 345                 350

Glu Ala Ala Ala Leu Ser Gly Asp Val Ala Val Lys Ala Ala Ser Leu
         355                 360                 365

Gly Gly Gly Gly Gly Gly Val Pro Ser Ala Pro Leu Gly Ser Ala
             370                 375                 380

Ile Gly Gly Ala Glu Ser Val Arg Pro Ala Gly Ala Gly Asp Ile Ala
385                 390                 395                 400

Gly Leu Gly Gln Gly Arg Ala Gly Gly Ala Ala Leu Gly Gly Gly
                 405                 410                 415

Gly Met Gly Met Pro Met Gly Ala Ala His Gln Gly Gln Gly Gly Ala
             420                 425                 430

Lys Ser Lys Gly Ser Gln Gln Glu Asp Glu Ala Leu Tyr Thr Glu Asp
```

```
            435                 440                 445
Arg Ala Trp Thr Glu Ala Val Ile Gly Asn Arg Arg Gln Asp Ser
450                 455                 460
Lys Glu Ser Lys Gly Ser Thr Glu Gln Gln Trp Asn Phe Ala Gly Ile
465                 470                 475                 480
Glu Ala Ala Ala Ser Ala Ile Gln Gly Asn Val Thr Ser Ile His Ser
                    485                 490                 495
Leu Leu Asp Glu Gly Lys Gln Ser Leu Thr Lys Leu Ala Ala Ala Trp
                500                 505                 510
Gly Gly Ser Gly Ser Glu Ala Tyr Gln Gly Val Gln Gln Lys Trp Asp
            515                 520                 525
Ala Thr Ala Thr Glu Leu Asn Asn Ala Leu Gln Asn Leu Ala Arg Thr
        530                 535                 540
Ile Ser Glu Ala Gly Gln Ala Met Ala Ser Thr Glu Gly Asn Val Thr
545                 550                 555                 560
Gly Met Phe Ala Glu Phe Asp Leu Pro Gly Asn Asp Phe Asp Ser Asn
                565                 570                 575
Asp Phe Asp Ala Val Asp Leu Trp Gly Ala Asp Gly Ala Glu Gly Trp
                580                 585                 590
Thr Ala Asp Pro Ile Ile Gly Val Gly Ser Ala Ala Thr Pro Asp Thr
            595                 600                 605
Gly Pro Asp Leu Asp Asn Ala His Gly Gln Ala Glu Thr Asp Thr Glu
        610                 615                 620
Gln Glu Ile Ala Leu Phe Thr Val Thr Asn Pro Pro Arg Thr Val Ser
625                 630                 635                 640
Val Ser Thr Leu Met Asp Gly Arg Ile Asp His Val Glu Leu Ser Ala
                645                 650                 655
Arg Val Ala Trp Met Ser Glu Ser Gln Leu Ala Ser Glu Ile Leu Val
                660                 665                 670
Ile Ala Asp Leu Ala Arg Gln Lys Ala Gln Ser Ala Gln Tyr Ala Phe
                675                 680                 685
Ile Leu Asp Arg Met Ser Gln Gln Val Asp Ala Asp Glu His Arg Val
            690                 695                 700
Ala Leu Leu Arg Lys Thr Val Gly Glu Thr Trp Gly Leu Pro Ser Pro
705                 710                 715                 720
Glu Glu Ala Ala Ala Glu Ala Glu Val Phe Ala Thr Arg Tyr Ser
                725                 730                 735
Asp Asp Ser Pro Ala Pro Asp Glu Ser Asp Pro Trp Thr Glu Asn
                740                 745                 750
Leu Thr Val Gln Pro Glu Arg Leu Gly Val Leu Ala Ser His His Asp
            755                 760                 765
Asn Ala Ala Val Asp Ala Ser Ser Gly Val Glu Ala Ala Gly Leu
        770                 775                 780
Gly Glu Ser Val Ala Ile Thr His Gly Pro Tyr Ser Ser Gln Phe Asn
785                 790                 795                 800
Asp Thr Leu Asn Val Tyr Leu Thr Ala His Asn Ala Leu Gly Ser Ser
                805                 810                 815
Leu His Thr Ala Gly Val Asp Leu Ala Lys Ser Leu Arg Ile Ala Ala
                820                 825                 830
Lys Ile Tyr Ser Glu Ala Asp Glu Ala Trp Arg Lys Ala Ile Asp Gly
            835                 840                 845
Leu Phe Thr Ser Arg Ala Phe Ile Ile Asp Pro Thr Ile Ser Ala Ile
        850                 855                 860
```

```
Asp Gly Leu Tyr Asp Leu Leu Gly Ile Gly Ile Pro Asn Gln Gly Gly
865                 870                 875                 880

Ile Leu Tyr Ser Ser Leu Glu Tyr Phe Glu Lys Ala Leu Glu Glu Leu
                885                 890                 895

Ala Ala Ala Phe Pro Gly Asp Gly Trp Leu Gly Ser Ala Ala Asp Lys
            900                 905                 910

Tyr Ala Gly Lys Asn Arg Asn His Val Asn Phe Phe Gln Glu Leu Ala
        915                 920                 925

Asp Leu Asp Arg Gln Leu Ile Ser Leu Ile His Asp Gln Ala Asn Ala
    930                 935                 940

Val Gln Thr Thr Arg Asp Ile Leu Glu Gly Ala Lys Lys Gly Leu Glu
945                 950                 955                 960

Phe Val Arg Pro Val Ala Val Asp Leu Thr Tyr Ile Pro Val Val Gly
                965                 970                 975

His Ala Leu Asp Val Ala Asp Ile Ile Lys Gly Thr Leu Gly Glu Val
            980                 985                 990

Trp Glu Phe Ile Thr Asn Ala Leu Asn Gly Leu Lys Glu Leu Trp Asp
        995                 1000                1005

Lys Leu Thr Gly Trp Val Thr Gly Leu Phe Ser Arg Gly Trp Ser
    1010                1015                1020

Asn Leu Glu Ser Phe Phe Ala Gly Val Pro Gly Leu Thr Gly Ala
    1025                1030                1035

Thr Ser Gly Leu Ser Gln Val Thr Gly Leu Phe Gly Ala Ala Gly
    1040                1045                1050

Leu Ser Ala Ser Ser Gly Leu Ala His Ala Asp Ser Leu Ala Ser
    1055                1060                1065

Ser Ala Ser Leu Pro Ala Leu Ala Gly Ile Gly Gly Gly Ser Gly
    1070                1075                1080

Phe Gly Gly Leu Pro Ser Leu Ala Gln Val His Ala Ala Ser Thr
    1085                1090                1095

Arg Gln Ala Leu Arg Pro Arg Ala Asp Gly Pro Val Gly Ala Ala
    1100                1105                1110

Ala Glu Gln Val Gly Gly Gln Ser Gln Leu Val Ser Ala Gln Gly
    1115                1120                1125

Ser Gln Gly Met Gly Gly Pro Val Gly Met Gly Gly Met His Pro
    1130                1135                1140

Ser Ser Gly Ala Ser Lys Gly Thr Thr Thr Lys Lys Tyr Ser Glu
    1145                1150                1155

Gly Ala Ala Ala Gly Thr Glu Asp Ala Glu Arg Ala Pro Val Glu
    1160                1165                1170

Ala Asp Ala Gly Gly Gly Gln Lys Val Leu Val Arg Asn Val Val
    1175                1180                1185

Ser Thr Thr Phe Ala Ala Arg Leu Asn Arg Leu Phe Asp Thr Val
    1190                1195                1200

Tyr Pro Pro Gly Arg Gly Pro His Thr Ser Ala Glu Val Ile Ala
    1205                1210                1215

Ala Leu Lys Ala Glu Gly Ile Thr Met Ser Ala Pro Tyr Leu Ser
    1220                1225                1230

Gln Leu Arg Ser Gly Asn Arg Thr Asn Pro Ser Gly Ala Thr Met
    1235                1240                1245

Ala Ala Leu Ala Asn Phe Phe Arg Ile Lys Ala Ala Tyr Phe Thr
    1250                1255                1260
```

```
Asp Asp Glu Tyr Tyr Glu Lys Leu Asp Lys Glu Leu Gln Trp Leu
    1265                1270                1275

Ser Thr Met Arg Asp Asp Gly Val Arg Arg Ile Ala Gln Arg Ala
    1280                1285                1290

His Gly Leu Pro Ser Ala Ala Gln Gln Lys Val Leu Asp Arg Ile
    1295                1300                1305

Asp Glu Leu Arg Arg Ala Glu Gly Ile Asp Ala
    1310                1315

<210> SEQ ID NO 8
<211> LENGTH: 99
<212> TYPE: PRT
<213> ORGANISM: Mycobacterium tuberculosis

<400> SEQUENCE: 8

Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
                20                  25                  30

Thr Ser Val Thr Gly Leu Val Pro Ala Gly Ala Asp Glu Val Ser Ala
            35                  40                  45

Gln Ala Ala Thr Ala Phe Thr Ser Glu Gly Ile Gln Leu Leu Ala Ser
        50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala Glu

<210> SEQ ID NO 9
<211> LENGTH: 518
<212> TYPE: PRT
<213> ORGANISM: Mycobacterium tuberculosis

<400> SEQUENCE: 9

Met His His His His His His Gly Gly Ser Thr Glu Gln Gln Trp Asn
1               5                   10                  15

Phe Ala Gly Ile Glu Ala Ala Ala Ser Ala Ile Gln Gly Asn Val Thr
                20                  25                  30

Ser Ile His Ser Leu Leu Asp Glu Gly Lys Gln Ser Leu Thr Lys Leu
            35                  40                  45

Ala Ala Ala Trp Gly Gly Ser Gly Ser Glu Ala Tyr Gln Gly Val Gln
        50                  55                  60

Gln Lys Trp Asp Ala Thr Ala Thr Glu Leu Asn Asn Ala Leu Gln Asn
65                  70                  75                  80

Leu Ala Arg Thr Ile Ser Glu Ala Gly Gln Ala Met Ala Ser Thr Glu
                85                  90                  95

Gly Asn Val Thr Gly Met Phe Ala Glu Phe Asp Leu Pro Gly Asn Asp
            100                 105                 110

Phe Asp Ser Asn Asp Phe Asp Ala Val Asp Leu Trp Gly Ala Asp Gly
        115                 120                 125

Ala Glu Gly Trp Thr Ala Asp Pro Ile Ile Gly Val Gly Ser Ala Ala
    130                 135                 140

Thr Pro Asp Thr Gly Pro Asp Leu Asp Asn Ala His Gly Gln Ala Glu
145                 150                 155                 160

Thr Asp Thr Glu Gln Glu Ile Ala Leu Phe Thr Val Thr Asn Pro Pro
```

-continued

```
                165                 170                 175
Arg Thr Val Ser Val Ser Thr Leu Met Asp Gly Arg Ile Asp His Val
                180                 185                 190

Glu Leu Ser Ala Arg Val Ala Trp Met Ser Glu Ser Gln Leu Ala Ser
                195                 200                 205

Glu Ile Leu Val Ile Ala Asp Leu Ala Arg Gln Lys Ala Gln Ser Ala
            210                 215                 220

Gln Tyr Ala Phe Ile Leu Asp Arg Met Ser Gln Val Asp Ala Asp
225                 230                 235                 240

Glu His Arg Val Ala Leu Leu Arg Lys Thr Val Gly Glu Thr Trp Gly
                245                 250                 255

Leu Pro Ser Pro Glu Ala Ala Ala Glu Ala Glu Val Phe Ala
            260                 265                 270

Thr Arg Tyr Ser Asp Asp Ser Pro Ala Pro Asp Glu Ser Asp Pro
            275                 280                 285

Trp Ser Thr Thr Phe Ala Ala Arg Leu Asn Arg Leu Phe Asp Thr Val
            290                 295                 300

Tyr Pro Pro Gly Arg Gly Pro His Thr Ser Ala Glu Val Ile Ala Ala
305                 310                 315                 320

Leu Lys Ala Glu Gly Ile Thr Met Ser Ala Pro Tyr Leu Ser Gln Leu
                325                 330                 335

Arg Ser Gly Asn Arg Thr Asn Pro Ser Gly Ala Thr Met Ala Ala Leu
            340                 345                 350

Ala Asn Phe Phe Arg Ile Lys Ala Ala Tyr Phe Thr Asp Asp Glu Tyr
                355                 360                 365

Tyr Glu Lys Leu Asp Lys Glu Leu Gln Trp Leu Ser Thr Met Arg Asp
370                 375                 380

Asp Gly Val Arg Arg Ile Ala Gln Arg Ala His Gly Leu Pro Ser Ala
385                 390                 395                 400

Ala Gln Gln Lys Val Leu Asp Arg Ile Asp Glu Leu Arg Arg Ala Glu
                405                 410                 415

Gly Ile Asp Ala Glu Lys Met Ser His Asp Pro Ile Ala Ala Asp Ile
                420                 425                 430

Gly Thr Gln Val Ser Asp Asn Ala Leu His Gly Val Thr Ala Gly Ser
            435                 440                 445

Thr Ala Leu Thr Ser Val Thr Gly Leu Val Pro Ala Gly Ala Asp Glu
            450                 455                 460

Val Ser Ala Gln Ala Ala Thr Ala Phe Thr Ser Glu Gly Ile Gln Leu
465                 470                 475                 480

Leu Ala Ser Asn Ala Ser Ala Gln Asp Gln Leu His Arg Ala Gly Glu
                485                 490                 495

Ala Val Gln Asp Val Ala Arg Thr Tyr Ser Gln Ile Asp Asp Gly Ala
            500                 505                 510

Ala Gly Val Phe Ala Glu
            515
```

<210> SEQ ID NO 10
<211> LENGTH: 1217
<212> TYPE: PRT
<213> ORGANISM: Mycobacterium tuberculosis

<400> SEQUENCE: 10

```
Met His His His His His Gly Ser Thr Gln Ser Gln Thr Val Thr
1               5                   10                  15
```

Val Asp Gln Gln Glu Ile Leu Asn Arg Ala Asn Glu Val Glu Ala Pro
            20                  25                  30

Met Ala Asp Pro Pro Thr Asp Val Pro Ile Thr Pro Ser Glu Leu Thr
        35                  40                  45

Ala Ala Lys Asn Ala Ala Gln Gln Leu Val Leu Ser Ala Asp Asn Met
    50                  55                  60

Arg Glu Tyr Leu Ala Ala Gly Ala Lys Glu Arg Gln Arg Leu Ala Thr
65                  70                  75                  80

Ser Leu Arg Asn Ala Ala Lys Ala Tyr Gly Glu Val Asp Glu Glu Ala
                85                  90                  95

Ala Thr Ala Leu Asp Asn Asp Gly Glu Gly Thr Val Gln Ala Glu Ser
            100                 105                 110

Ala Gly Ala Val Gly Gly Asp Ser Ser Ala Glu Leu Thr Asp Thr Pro
        115                 120                 125

Arg Val Ala Thr Ala Gly Glu Pro Asn Phe Met Asp Leu Lys Glu Ala
    130                 135                 140

Ala Arg Lys Leu Glu Thr Gly Asp Gln Gly Ala Ser Leu Ala His Phe
145                 150                 155                 160

Ala Asp Gly Trp Asn Thr Phe Asn Leu Thr Leu Gln Gly Asp Val Lys
                165                 170                 175

Arg Phe Arg Gly Phe Asp Asn Trp Glu Gly Asp Ala Ala Thr Ala Ser
            180                 185                 190

Glu Ala Ser Leu Asp Gln Arg Gln Trp Ile Leu His Met Ala Lys
        195                 200                 205

Leu Ser Ala Ala Met Ala Lys Gln Ala Gln Tyr Val Ala Gln Leu His
    210                 215                 220

Val Trp Ala Arg Arg Glu His Pro Thr Tyr Glu Asp Ile Val Gly Leu
225                 230                 235                 240

Glu Arg Leu Tyr Ala Glu Asn Pro Ser Ala Arg Asp Gln Ile Leu Pro
                245                 250                 255

Val Tyr Ala Glu Tyr Gln Gln Arg Ser Glu Lys Val Leu Thr Glu Tyr
            260                 265                 270

Asn Asn Lys Ala Ala Leu Glu Pro Val Asn Pro Pro Lys Pro Pro Pro
        275                 280                 285

Ala Ile Lys Ile Asp Pro Pro Pro Pro Gln Glu Gln Gly Leu Ile
    290                 295                 300

Pro Gly Phe Leu Met Pro Pro Ser Asp Gly Ser Gly Val Thr Pro Gly
305                 310                 315                 320

Thr Gly Met Pro Ala Ala Pro Met Val Pro Pro Thr Gly Ser Pro Gly
                325                 330                 335

Gly Gly Leu Pro Ala Asp Thr Ala Ala Gln Leu Thr Ser Ala Gly Arg
            340                 345                 350

Glu Ala Ala Ala Leu Ser Gly Asp Val Ala Val Lys Ala Ala Ser Leu
        355                 360                 365

Gly Gly Gly Gly Gly Gly Val Pro Ser Ala Pro Leu Gly Ser Ala
    370                 375                 380

Ile Gly Gly Ala Glu Ser Val Arg Pro Ala Gly Ala Gly Asp Ile Ala
385                 390                 395                 400

Gly Leu Gly Gln Gly Arg Ala Gly Gly Ala Ala Leu Gly Gly Gly
                405                 410                 415

Gly Met Gly Met Pro Met Gly Ala Ala His Gln Gly Gln Gly Gly Ala
            420                 425                 430

Lys Ser Lys Gly Ser Gln Gln Glu Asp Glu Ala Leu Tyr Thr Glu Asp

```
            435                 440                 445
Arg Ala Trp Thr Glu Ala Val Ile Gly Asn Arg Arg Gln Asp Ser
450                 455                 460
Lys Glu Ser Lys Gly Ser Thr Glu Gln Gln Trp Asn Phe Ala Gly Ile
465                 470                 475                 480
Glu Ala Ala Ala Ser Ala Ile Gln Gly Asn Val Thr Ser Ile His Ser
                    485                 490                 495
Leu Leu Asp Glu Gly Lys Gln Ser Leu Thr Lys Leu Ala Ala Ala Trp
                500                 505                 510
Gly Gly Ser Gly Ser Glu Ala Tyr Gln Gly Val Gln Gln Lys Trp Asp
            515                 520                 525
Ala Thr Ala Thr Glu Leu Asn Asn Ala Leu Gln Asn Leu Ala Arg Thr
530                 535                 540
Ile Ser Glu Ala Gly Gln Ala Met Ala Ser Thr Glu Gly Asn Val Thr
545                 550                 555                 560
Gly Met Phe Ala Glu Phe Asp Leu Pro Gly Asn Asp Phe Asp Ser Asn
                    565                 570                 575
Asp Phe Asp Ala Val Asp Leu Trp Gly Ala Asp Gly Ala Glu Gly Trp
                580                 585                 590
Thr Ala Asp Pro Ile Ile Gly Val Gly Ser Ala Ala Thr Pro Asp Thr
            595                 600                 605
Gly Pro Asp Leu Asp Asn Ala His Gly Gln Ala Glu Thr Asp Thr Glu
610                 615                 620
Gln Glu Ile Ala Leu Phe Thr Val Thr Asn Pro Pro Arg Thr Val Ser
625                 630                 635                 640
Val Ser Thr Leu Met Asp Gly Arg Ile Asp His Val Glu Leu Ser Ala
                    645                 650                 655
Arg Val Ala Trp Met Ser Glu Ser Gln Leu Ala Ser Glu Ile Leu Val
                660                 665                 670
Ile Ala Asp Leu Ala Arg Gln Lys Ala Gln Ser Ala Gln Tyr Ala Phe
            675                 680                 685
Ile Leu Asp Arg Met Ser Gln Gln Val Asp Ala Asp Glu His Arg Val
            690                 695                 700
Ala Leu Leu Arg Lys Thr Val Gly Glu Thr Trp Gly Leu Pro Ser Pro
705                 710                 715                 720
Glu Glu Ala Ala Ala Glu Ala Glu Val Phe Ala Thr Arg Tyr Ser
                    725                 730                 735
Asp Asp Ser Pro Ala Pro Asp Asp Glu Ser Asp Pro Trp Ser Arg Ala
                740                 745                 750
Phe Ile Ile Asp Pro Thr Ile Ser Ala Ile Asp Gly Leu Tyr Asp Leu
            755                 760                 765
Leu Gly Ile Gly Ile Pro Asn Gln Gly Gly Ile Leu Tyr Ser Ser Leu
            770                 775                 780
Glu Tyr Phe Glu Lys Ala Leu Glu Glu Leu Ala Ala Ala Phe Pro Gly
785                 790                 795                 800
Asp Gly Trp Leu Gly Ser Ala Ala Asp Lys Tyr Ala Gly Lys Asn Arg
                805                 810                 815
Asn His Val Asn Phe Phe Gln Glu Leu Ala Asp Leu Asp Arg Gln Leu
                820                 825                 830
Ile Ser Leu Ile His Asp Gln Ala Asn Ala Val Gln Thr Thr Arg Asp
            835                 840                 845
Ile Leu Glu Gly Ala Lys Lys Gly Leu Glu Phe Val Arg Pro Val Ala
850                 855                 860
```

Val Asp Leu Thr Tyr Ile Pro Val Val Gly His Ala Leu Asp Val Ala
865                 870                 875                 880

Asp Ile Ile Lys Gly Thr Leu Gly Glu Val Trp Glu Phe Ile Thr Asn
            885                 890                 895

Ala Leu Asn Gly Leu Lys Glu Leu Trp Asp Lys Leu Thr Gly Trp Val
            900                 905                 910

Thr Gly Leu Phe Ser Arg Gly Trp Ser Asn Leu Glu Ser Phe Phe Ala
        915                 920                 925

Gly Val Pro Gly Leu Thr Gly Ala Thr Ser Gly Leu Ser Gln Val Thr
        930                 935                 940

Gly Leu Phe Gly Ala Ala Gly Leu Ser Ala Ser Ser Gly Leu Ala His
945                 950                 955                 960

Ala Asp Ser Leu Ala Ser Ser Ala Ser Leu Pro Ala Leu Ala Gly Ile
            965                 970                 975

Gly Gly Gly Ser Gly Phe Gly Gly Leu Pro Ser Leu Ala Gln Val His
            980                 985                 990

Ala Ala Ser Thr Arg Gln Ala Leu Arg Pro Arg Ala Asp Gly Pro Val
            995                 1000                1005

Gly Ala Ala Ala Glu Gln Val Gly Gly Gln Ser Gln Leu Val Ser
    1010                1015                1020

Ala Gln Gly Ser Gln Gly Met Gly Gly Pro Val Gly Met Gly Gly
    1025                1030                1035

Met His Pro Ser Ser Gly Ala Ser Lys Gly Thr Thr Thr Lys Lys
    1040                1045                1050

Tyr Ser Glu Gly Ala Ala Ala Gly Thr Glu Asp Ala Glu Arg Ala
    1055                1060                1065

Pro Val Glu Ala Asp Ala Gly Gly Gly Gln Lys Val Leu Val Arg
    1070                1075                1080

Asn Val Val Ser Thr Thr Phe Ala Ala Arg Leu Asn Arg Leu Phe
    1085                1090                1095

Asp Thr Val Tyr Pro Pro Gly Arg Gly Pro His Thr Ser Ala Glu
    1100                1105                1110

Val Ile Ala Ala Leu Lys Ala Glu Gly Ile Thr Met Ser Ala Pro
    1115                1120                1125

Tyr Leu Ser Gln Leu Arg Ser Gly Asn Arg Thr Asn Pro Ser Gly
    1130                1135                1140

Ala Thr Met Ala Ala Leu Ala Asn Phe Phe Arg Ile Lys Ala Ala
    1145                1150                1155

Tyr Phe Thr Asp Asp Glu Tyr Tyr Glu Lys Leu Asp Lys Glu Leu
    1160                1165                1170

Gln Trp Leu Ser Thr Met Arg Asp Asp Gly Val Arg Arg Ile Ala
    1175                1180                1185

Gln Arg Ala His Gly Leu Pro Ser Ala Ala Gln Gln Lys Val Leu
    1190                1195                1200

Asp Arg Ile Asp Glu Leu Arg Arg Ala Glu Gly Ile Asp Ala
    1205                1210                1215

<210> SEQ ID NO 11
<211> LENGTH: 335
<212> TYPE: PRT
<213> ORGANISM: Mycobacterium tuberculosis

<400> SEQUENCE: 11

Met His His His His His His Gly Gly Ser Thr Glu Gln Gln Trp Asn

```
  1               5                  10                  15
    Phe Ala Gly Ile Glu Ala Ala Ser Ala Ile Gln Gly Asn Val Thr
                 20                  25                  30

Ser Ile His Ser Leu Leu Asp Glu Gly Lys Gln Ser Leu Thr Lys Leu
                 35                  40                  45

Ala Ala Ala Trp Gly Gly Ser Gly Ser Glu Ala Tyr Gln Gly Val Gln
         50                  55                  60

Gln Lys Trp Asp Ala Thr Ala Thr Glu Leu Asn Asn Ala Leu Gln Asn
    65                  70                  75                  80

Leu Ala Arg Thr Ile Ser Glu Ala Gly Gln Ala Met Ala Ser Thr Glu
                     85                  90                  95

Gly Asn Val Thr Gly Met Phe Ala Glu Phe Ser Thr Thr Phe Ala Ala
                    100                 105                 110

Arg Leu Asn Arg Leu Phe Asp Thr Val Tyr Pro Pro Gly Arg Gly Pro
                    115                 120                 125

His Thr Ser Ala Glu Val Ile Ala Ala Leu Lys Ala Glu Gly Ile Thr
                130                 135                 140

Met Ser Ala Pro Tyr Leu Ser Gln Leu Arg Ser Gly Asn Arg Thr Asn
    145                 150                 155                 160

Pro Ser Gly Ala Thr Met Ala Ala Leu Ala Asn Phe Phe Arg Ile Lys
                    165                 170                 175

Ala Ala Tyr Phe Thr Asp Asp Glu Tyr Tyr Glu Lys Leu Asp Lys Glu
                    180                 185                 190

Leu Gln Trp Leu Ser Thr Met Arg Asp Asp Gly Val Arg Arg Ile Ala
                    195                 200                 205

Gln Arg Ala His Gly Leu Pro Ser Ala Ala Gln Gln Lys Val Leu Asp
    210                 215                 220

Arg Ile Asp Glu Leu Arg Arg Ala Glu Gly Ile Asp Ala Glu Lys Met
    225                 230                 235                 240

Ser His Asp Pro Ile Ala Ala Asp Ile Gly Thr Gln Val Ser Asp Asn
                    245                 250                 255

Ala Leu His Gly Val Thr Ala Gly Ser Thr Ala Leu Thr Ser Val Thr
                    260                 265                 270

Gly Leu Val Pro Ala Gly Ala Asp Glu Val Ser Ala Gln Ala Ala Thr
                275                 280                 285

Ala Phe Thr Ser Glu Gly Ile Gln Leu Leu Ala Ser Asn Ala Ser Ala
                290                 295                 300

Gln Asp Gln Leu His Arg Ala Gly Glu Ala Val Gln Asp Val Ala Arg
    305                 310                 315                 320

Thr Tyr Ser Gln Ile Asp Asp Gly Ala Ala Gly Val Phe Ala Glu
                    325                 330                 335

<210> SEQ ID NO 12
<211> LENGTH: 1034
<212> TYPE: PRT
<213> ORGANISM: Mycobacterium tuberculosis

<400> SEQUENCE: 12

Met His His His His His Gly Ser Thr Gln Ser Gln Thr Val Thr
1               5                  10                  15

Val Asp Gln Gln Glu Ile Leu Asn Arg Ala Asn Glu Val Glu Ala Pro
                20                  25                  30

Met Ala Asp Pro Pro Thr Asp Val Pro Ile Thr Pro Ser Glu Leu Thr
                35                  40                  45
```

-continued

```
Ala Ala Lys Asn Ala Ala Gln Gln Leu Val Leu Ser Ala Asp Asn Met
    50                  55                  60
Arg Glu Tyr Leu Ala Ala Gly Ala Lys Glu Arg Gln Arg Leu Ala Thr
65                  70                  75                  80
Ser Leu Arg Asn Ala Ala Lys Ala Tyr Gly Glu Val Asp Glu Ala
                85                  90                  95
Ala Thr Ala Leu Asp Asn Asp Gly Glu Gly Thr Val Gln Ala Glu Ser
                100                 105                 110
Ala Gly Ala Val Gly Gly Asp Ser Ser Ala Glu Leu Thr Asp Thr Pro
                115                 120                 125
Arg Val Ala Thr Ala Gly Glu Pro Asn Phe Met Asp Leu Lys Glu Ala
130                 135                 140
Ala Arg Lys Leu Glu Thr Gly Asp Gln Gly Ala Ser Leu Ala His Phe
145                 150                 155                 160
Ala Asp Gly Trp Asn Thr Phe Asn Leu Thr Leu Gln Gly Asp Val Lys
                165                 170                 175
Arg Phe Arg Gly Phe Asp Asn Trp Glu Gly Asp Ala Ala Thr Ala Ser
                180                 185                 190
Glu Ala Ser Leu Asp Gln Gln Arg Gln Trp Ile Leu His Met Ala Lys
                195                 200                 205
Leu Ser Ala Ala Met Ala Lys Gln Ala Gln Tyr Val Ala Gln Leu His
    210                 215                 220
Val Trp Ala Arg Arg Glu His Pro Thr Tyr Glu Asp Ile Val Gly Leu
225                 230                 235                 240
Glu Arg Leu Tyr Ala Glu Asn Pro Ser Ala Arg Asp Gln Ile Leu Pro
                245                 250                 255
Val Tyr Ala Glu Tyr Gln Gln Arg Ser Glu Lys Val Leu Thr Glu Tyr
                260                 265                 270
Asn Asn Lys Ala Ala Leu Glu Pro Val Asn Pro Pro Lys Pro Pro Pro
                275                 280                 285
Ala Ile Lys Ile Asp Pro Pro Pro Gln Glu Gln Gly Leu Ile
    290                 295                 300
Pro Gly Phe Leu Met Pro Pro Ser Asp Gly Ser Gly Val Thr Pro Gly
305                 310                 315                 320
Thr Gly Met Pro Ala Ala Pro Met Val Pro Thr Gly Ser Pro Gly
                325                 330                 335
Gly Gly Leu Pro Ala Asp Thr Ala Ala Gln Leu Thr Ser Ala Gly Arg
                340                 345                 350
Glu Ala Ala Ala Leu Ser Gly Asp Val Ala Val Lys Ala Ala Ser Leu
                355                 360                 365
Gly Gly Gly Gly Gly Gly Val Pro Ser Ala Pro Leu Gly Ser Ala
                370                 375                 380
Ile Gly Gly Ala Glu Ser Val Arg Pro Ala Gly Ala Gly Asp Ile Ala
385                 390                 395                 400
Gly Leu Gly Gln Gly Arg Ala Gly Gly Ala Ala Leu Gly Gly
                405                 410                 415
Gly Met Gly Met Pro Met Gly Ala Ala His Gln Gly Gln Gly Ala
                420                 425                 430
Lys Ser Lys Gly Ser Gln Gln Glu Asp Glu Ala Leu Tyr Thr Glu Asp
                435                 440                 445
Arg Ala Trp Thr Glu Ala Val Ile Gly Asn Arg Arg Gln Asp Ser
450                 455                 460
Lys Glu Ser Lys Gly Ser Thr Glu Gln Gln Trp Asn Phe Ala Gly Ile
```

```
                465                 470                 475                 480
            Glu Ala Ala Ala Ser Ala Ile Gln Gly Asn Val Thr Ser Ile His Ser
                                485                 490                 495
            Leu Leu Asp Glu Gly Lys Gln Ser Leu Thr Lys Leu Ala Ala Ala Trp
                            500                 505                 510
            Gly Gly Ser Gly Ser Glu Ala Tyr Gln Gly Val Gln Gln Lys Trp Asp
                        515                 520                 525
            Ala Thr Ala Thr Glu Leu Asn Asn Ala Leu Gln Asn Leu Ala Arg Thr
                    530                 535                 540
            Ile Ser Glu Ala Gly Gln Ala Met Ala Ser Thr Glu Gly Asn Val Thr
            545                 550                 555                 560
            Gly Met Phe Ala Glu Phe Ser Arg Ala Phe Ile Ile Asp Pro Thr Ile
                                565                 570                 575
            Ser Ala Ile Asp Gly Leu Tyr Asp Leu Leu Gly Ile Gly Ile Pro Asn
                            580                 585                 590
            Gln Gly Gly Ile Leu Tyr Ser Ser Leu Glu Tyr Phe Glu Lys Ala Leu
                        595                 600                 605
            Glu Glu Leu Ala Ala Ala Phe Pro Gly Asp Gly Trp Leu Gly Ser Ala
                    610                 615                 620
            Ala Asp Lys Tyr Ala Gly Lys Asn Arg Asn His Val Asn Phe Phe Gln
            625                 630                 635                 640
            Glu Leu Ala Asp Leu Asp Arg Gln Leu Ile Ser Leu Ile His Asp Gln
                                645                 650                 655
            Ala Asn Ala Val Gln Thr Thr Arg Asp Ile Leu Glu Gly Ala Lys Lys
                            660                 665                 670
            Gly Leu Glu Phe Val Arg Pro Val Ala Val Asp Leu Thr Tyr Ile Pro
                        675                 680                 685
            Val Val Gly His Ala Leu Asp Val Ala Asp Ile Ile Lys Gly Thr Leu
                    690                 695                 700
            Gly Glu Val Trp Glu Phe Ile Thr Asn Ala Leu Asn Gly Leu Lys Glu
            705                 710                 715                 720
            Leu Trp Asp Lys Leu Thr Gly Trp Val Thr Gly Leu Phe Ser Arg Gly
                            725                 730                 735
            Trp Ser Asn Leu Glu Ser Phe Phe Ala Gly Val Pro Gly Leu Thr Gly
                        740                 745                 750
            Ala Thr Ser Gly Leu Ser Gln Val Thr Gly Leu Phe Gly Ala Ala Gly
                    755                 760                 765
            Leu Ser Ala Ser Ser Gly Leu Ala His Ala Asp Ser Leu Ala Ser Ser
                770                 775                 780
            Ala Ser Leu Pro Ala Leu Ala Gly Ile Gly Gly Ser Gly Phe Gly
            785                 790                 795                 800
            Gly Leu Pro Ser Leu Ala Gln Val His Ala Ala Ser Thr Arg Gln Ala
                            805                 810                 815
            Leu Arg Pro Arg Ala Asp Gly Pro Val Gly Ala Ala Glu Gln Val
                        820                 825                 830
            Gly Gly Gln Ser Gln Leu Val Ser Ala Gln Gly Ser Gln Gly Met Gly
                    835                 840                 845
            Gly Pro Val Gly Met Gly Met His Pro Ser Ser Gly Ala Ser Lys
                850                 855                 860
            Gly Thr Thr Thr Lys Lys Tyr Ser Glu Gly Ala Ala Ala Gly Thr Glu
            865                 870                 875                 880
            Asp Ala Glu Arg Ala Pro Val Glu Ala Asp Ala Gly Gly Gly Gln Lys
                            885                 890                 895
```

```
Val Leu Val Arg Asn Val Val Ser Thr Thr Phe Ala Ala Arg Leu Asn
            900                 905                 910

Arg Leu Phe Asp Thr Val Tyr Pro Pro Gly Arg Gly Pro His Thr Ser
            915                 920                 925

Ala Glu Val Ile Ala Ala Leu Lys Ala Glu Gly Ile Thr Met Ser Ala
            930                 935                 940

Pro Tyr Leu Ser Gln Leu Arg Ser Gly Asn Arg Thr Asn Pro Ser Gly
945                 950                 955                 960

Ala Thr Met Ala Ala Leu Ala Asn Phe Phe Arg Ile Lys Ala Ala Tyr
            965                 970                 975

Phe Thr Asp Asp Glu Tyr Tyr Glu Lys Leu Asp Lys Glu Leu Gln Trp
            980                 985                 990

Leu Ser Thr Met Arg Asp Asp Gly Val Arg Arg Ile Ala Gln Arg Ala
            995                 1000                1005

His Gly Leu Pro Ser Ala Ala Gln Gln Lys Val Leu Asp Arg Ile
            1010                1015                1020

Asp Glu Leu Arg Arg Ala Glu Gly Ile Asp Ala
            1025                1030

<210> SEQ ID NO 13
<211> LENGTH: 697
<212> TYPE: PRT
<213> ORGANISM: Mycobacterium tuberculosis

<400> SEQUENCE: 13

Met His His His His His His Gly Ser Thr Gln Ser Gln Thr Val Thr
1               5                   10                  15

Val Asp Gln Gln Glu Ile Leu Asn Arg Ala Asn Glu Val Glu Ala Pro
            20                  25                  30

Met Ala Asp Pro Pro Thr Asp Val Pro Ile Thr Pro Ser Glu Leu Thr
        35                  40                  45

Ala Ala Lys Asn Ala Ala Gln Gln Leu Val Leu Ser Ala Asp Asn Met
    50                  55                  60

Arg Glu Tyr Leu Ala Ala Gly Ala Lys Glu Arg Gln Arg Leu Ala Thr
65                  70                  75                  80

Ser Leu Arg Asn Ala Ala Lys Ala Tyr Gly Glu Val Asp Glu Glu Ala
                85                  90                  95

Ala Thr Ala Leu Asp Asn Asp Gly Glu Gly Thr Val Gln Ala Glu Ser
            100                 105                 110

Ala Gly Ala Val Gly Gly Asp Ser Ser Ala Glu Leu Thr Asp Thr Pro
        115                 120                 125

Arg Val Ala Thr Ala Gly Glu Pro Asn Phe Met Asp Leu Lys Glu Ala
    130                 135                 140

Ala Arg Lys Leu Glu Thr Gly Asp Gln Gly Ala Ser Leu Ala His Phe
145                 150                 155                 160

Ala Asp Gly Trp Asn Thr Phe Asn Leu Thr Leu Gln Gly Asp Val Lys
                165                 170                 175

Arg Phe Arg Gly Phe Asp Asn Trp Glu Gly Asp Ala Ala Thr Ala Ser
            180                 185                 190

Glu Ala Ser Leu Asp Gln Gln Arg Gln Trp Ile Leu His Met Ala Lys
        195                 200                 205

Leu Ser Ala Ala Met Ala Lys Gln Ala Gln Tyr Val Ala Gln Leu His
    210                 215                 220

Val Trp Ala Arg Arg Glu His Pro Thr Tyr Glu Asp Ile Val Gly Leu
```

```
            225                 230                 235                 240
Glu Arg Leu Tyr Ala Glu Asn Pro Ser Ala Arg Asp Gln Ile Leu Pro
                    245                 250                 255

Val Tyr Ala Glu Tyr Gln Gln Arg Ser Glu Lys Val Leu Thr Glu Tyr
                    260                 265                 270

Asn Asn Lys Ala Ala Leu Glu Pro Val Asn Pro Lys Pro Pro Pro
                275                 280                 285

Ala Ile Lys Ile Asp Pro Pro Pro Pro Gln Glu Gln Gly Leu Ile
            290                 295                 300

Pro Gly Phe Leu Met Pro Pro Ser Asp Gly Ser Gly Val Thr Pro Gly
305                 310                 315                 320

Thr Gly Met Pro Ala Ala Pro Met Val Pro Thr Gly Ser Pro Gly
                    325                 330                 335

Gly Gly Leu Pro Ala Asp Thr Ala Ala Gln Leu Thr Ser Ala Gly Arg
                340                 345                 350

Glu Ala Ala Ala Leu Ser Gly Asp Val Ala Val Lys Ala Ala Ser Leu
                355                 360                 365

Gly Gly Gly Gly Gly Gly Val Pro Ser Ala Pro Leu Gly Ser Ala
370                 375                 380

Ile Gly Gly Ala Glu Ser Val Arg Pro Ala Gly Ala Gly Asp Ile Ala
385                 390                 395                 400

Gly Leu Gly Gln Gly Arg Ala Gly Gly Ala Ala Leu Gly Gly Gly
                405                 410                 415

Gly Met Gly Met Pro Met Gly Ala Ala His Gln Gly Gln Gly Gly Ala
                420                 425                 430

Lys Ser Lys Gly Ser Gln Gln Glu Asp Glu Ala Leu Tyr Thr Glu Asp
            435                 440                 445

Arg Ala Trp Thr Glu Ala Val Ile Gly Asn Arg Arg Gln Asp Ser
450                 455                 460

Lys Glu Ser Lys Gly Ser Thr Glu Gln Gln Trp Asn Phe Ala Gly Ile
465                 470                 475                 480

Glu Ala Ala Ala Ser Ala Ile Gln Gly Asn Val Thr Ser Ile His Ser
                485                 490                 495

Leu Leu Asp Glu Gly Lys Gln Ser Leu Thr Lys Leu Ala Ala Ala Trp
            500                 505                 510

Gly Gly Ser Gly Ser Glu Ala Tyr Gln Gly Val Gln Gln Lys Trp Asp
            515                 520                 525

Ala Thr Ala Thr Glu Leu Asn Asn Ala Leu Gln Asn Leu Ala Arg Thr
            530                 535                 540

Ile Ser Glu Ala Gly Gln Ala Met Ala Ser Thr Glu Gly Asn Val Thr
545                 550                 555                 560

Gly Met Phe Ala Glu Phe Ser Thr Thr Phe Ala Ala Arg Leu Asn Arg
                565                 570                 575

Leu Phe Asp Thr Val Tyr Pro Pro Gly Arg Gly Pro His Thr Ser Ala
                580                 585                 590

Glu Val Ile Ala Ala Leu Lys Ala Glu Gly Ile Thr Met Ser Ala Pro
                595                 600                 605

Tyr Leu Ser Gln Leu Arg Ser Gly Asn Arg Thr Asn Pro Ser Gly Ala
            610                 615                 620

Thr Met Ala Ala Leu Ala Asn Phe Phe Arg Ile Lys Ala Ala Tyr Phe
625                 630                 635                 640

Thr Asp Asp Glu Tyr Tyr Glu Lys Leu Asp Lys Glu Leu Gln Trp Leu
                645                 650                 655
```

```
Ser Thr Met Arg Asp Asp Gly Val Arg Arg Ile Ala Gln Arg Ala His
        660                 665                 670

Gly Leu Pro Ser Ala Ala Gln Gln Lys Val Leu Asp Arg Ile Asp Glu
            675                 680                 685

Leu Arg Arg Ala Glu Gly Ile Asp Ala
    690                 695

<210> SEQ ID NO 14
<211> LENGTH: 572
<212> TYPE: PRT
<213> ORGANISM: Mycobacterium tuberculosis

<400> SEQUENCE: 14

Met His His His His His Thr Glu Gln Gln Trp Asn Phe Ala Gly
1               5                   10                  15

Ile Glu Ala Ala Ala Ser Ala Ile Gln Gly Asn Val Thr Ser Ile His
                20                  25                  30

Ser Leu Leu Asp Glu Gly Lys Gln Ser Leu Thr Lys Leu Ala Ala Ala
            35                  40                  45

Trp Gly Gly Ser Gly Ser Glu Ala Tyr Gln Gly Val Gln Gln Lys Trp
        50                  55                  60

Asp Ala Thr Ala Thr Glu Leu Asn Asn Ala Leu Gln Asn Leu Ala Arg
65                  70                  75                  80

Thr Ile Ser Glu Ala Gly Gln Ala Met Ala Ser Thr Glu Gly Asn Val
                85                  90                  95

Thr Gly Met Phe Ala Met Asp Leu Pro Gly Asn Asp Phe Asp Ser Asn
            100                 105                 110

Asp Phe Asp Ala Val Asp Leu Trp Gly Ala Asp Gly Ala Glu Gly Trp
        115                 120                 125

Thr Ala Asp Pro Ile Ile Gly Val Gly Ser Ala Ala Thr Pro Asp Thr
130                 135                 140

Gly Pro Asp Leu Asp Asn Ala His Gly Gln Ala Glu Thr Asp Thr Glu
145                 150                 155                 160

Gln Glu Ile Ala Leu Phe Thr Val Thr Asn Pro Pro Arg Thr Val Ser
                165                 170                 175

Val Ser Thr Leu Met Asp Gly Arg Ile Asp His Val Glu Leu Ser Ala
            180                 185                 190

Arg Val Ala Trp Met Ser Glu Ser Gln Leu Ala Ser Glu Ile Leu Val
        195                 200                 205

Ile Ala Asp Leu Ala Arg Gln Lys Ala Gln Ser Ala Gln Tyr Ala Phe
    210                 215                 220

Ile Leu Asp Arg Met Ser Gln Gln Val Asp Ala Asp Glu His Arg Val
225                 230                 235                 240

Ala Leu Leu Arg Lys Thr Val Gly Glu Thr Trp Gly Leu Pro Ser Pro
                245                 250                 255

Glu Glu Ala Ala Ala Glu Ala Glu Val Phe Ala Thr Arg Tyr Ser
            260                 265                 270

Asp Asp Ser Pro Ala Pro Asp Asp Glu Ser Asp Pro Trp Met Thr Glu
        275                 280                 285

Asn Leu Thr Val Gln Pro Glu Arg Leu Gly Val Leu Ala Ser His His
    290                 295                 300

Asp Asn Ala Ala Val Asp Ala Ser Ser Gly Val Glu Ala Ala Ala Gly
305                 310                 315                 320

Leu Gly Glu Ser Val Ala Ile Thr His Gly Pro Tyr Ser Ser Gln Phe
```

```
            325                 330                 335
Asn Asp Thr Leu Asn Met Ser Thr Thr Phe Ala Ala Arg Leu Asn Arg
            340                 345                 350

Leu Phe Asp Thr Val Tyr Pro Pro Gly Arg Gly Pro His Thr Ser Ala
            355                 360                 365

Glu Val Ile Ala Ala Leu Lys Ala Glu Gly Ile Thr Met Ser Ala Pro
            370                 375                 380

Tyr Leu Ser Gln Leu Arg Ser Gly Asn Arg Thr Asn Pro Ser Gly Ala
385                 390                 395                 400

Thr Met Ala Ala Leu Ala Asn Phe Phe Arg Ile Lys Ala Ala Tyr Phe
            405                 410                 415

Thr Asp Asp Glu Tyr Tyr Glu Lys Leu Asp Lys Glu Leu Gln Trp Leu
            420                 425                 430

Ser Thr Met Arg Asp Asp Gly Val Arg Arg Ile Ala Gln Arg Ala His
            435                 440                 445

Gly Leu Pro Ser Ala Ala Gln Gln Lys Val Leu Asp Arg Ile Asp Glu
450                 455                 460

Leu Arg Arg Ala Glu Gly Ile Asp Ala Met Glu Lys Met Ser His Asp
465                 470                 475                 480

Pro Ile Ala Ala Asp Ile Gly Thr Gln Val Ser Asp Asn Ala Leu His
                485                 490                 495

Gly Val Thr Ala Gly Ser Thr Ala Leu Thr Ser Val Thr Gly Leu Val
                500                 505                 510

Pro Ala Gly Ala Asp Glu Val Ser Ala Gln Ala Ala Thr Ala Phe Thr
            515                 520                 525

Ser Glu Gly Ile Gln Leu Leu Ala Ser Asn Ala Ser Ala Gln Asp Gln
530                 535                 540

Leu His Arg Ala Gly Glu Ala Val Gln Asp Val Ala Arg Thr Tyr Ser
545                 550                 555                 560

Gln Ile Asp Asp Gly Ala Ala Gly Val Phe Ala Glu
            565                 570

<210> SEQ ID NO 15
<211> LENGTH: 56
<212> TYPE: PRT
<213> ORGANISM: Mycobacterium tuberculosis

<400> SEQUENCE: 15

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
                20                  25                  30

Ala Ala Gly Leu Gly Glu Ser Val Ala Ile Thr His Gly Pro Tyr Ser
            35                  40                  45

Ser Gln Phe Asn Asp Thr Leu Asn
        50                  55
```

M. TUBERCULOSIS VACCINES

FIELD OF INVENTION

The present invention discloses new immunogenic compositions based on Esx-1 associated polypeptides derived from *M. tuberculosis*

GENERAL BACKGROUND

Immunity to *M. tuberculosis* is characterized by some basic features; specifically sensitized T lymphocytes mediates protection, and the most important mediator molecule seems to be interferon gamma (IFN-γ).

*M. tuberculosis* holds, as well as secretes, several proteins of potential relevance for the generation of a new TB vaccine. In 1998 Cole et al. published the complete genome sequence of *M. tuberculosis* and predicted the presence of approximately 4000 open reading frames[1]. However importantly, this sequence information cannot be used to predict if the DNA is translated and expressed as proteins in vivo. The genome sequence has been used extensively to design DNA arrays for RNA expression analysis and in proteome studies to identify expressed proteins. Even with the vaste amount of expression data and the significant improvement of in silico prediction tools it is still not possible to predictic with certainty that a given sequence will encode an immunogenic molecule. The only way to determine if a molecule is recognized by the immune system during or after an infection with *M. tuberculosis* is to produce the given molecule and test it in an appropriate assay as described herein.

Currently there are several new TB vaccines in clinical trials. However, they are primarily classical preventive vaccines based on a limited number of antigens expressed in the early stage of infection. As a direct consequence of the expression dynamic the epitope pattern that is presented to T cells changes radically over time—implicating how new vaccines should be designed. E.g. for the transiently expressed early antigen, Ag85B, two independent T cell transfer studies have shown that 3-4 weeks after infection, Ag85B is no longer being presented to T cells and as a result there is no Ag85B specific production of cytokine's, chemokine's etc. at this or later time points of the infection[2,3]. Thus, it is of limited value for a chronic disease that establish long-term co-existence with the host to vaccinate and induce memory T cells specific for epitopes in proteins that are only expressed during a brief period of the infection.

For vaccine development it is therefore vital to identify antigens that are highly expressed in the later stage of infection and among these select those that are immunogenic and can contribute to protection and include this special subset of proteins in TB vaccines. By doing so it is not only possible to improve vaccine potency and epitope coverage but also target latent infections.

Mycobacteria secretion systems are responsible for the export of proteins into the extracellular environment. The 6-kDa early secretory antigenic target of *Mycobacterium tuberculosis* (ESAT-6) and the 10-kDa culture filtrate antigen (CFP-10), are proteins secreted by the ESAT-6 secretion system 1 (ESX-1) and are among the most immunodominant *M. tuberculosis* (MTB) antigens. These attributes makes them important for tuberculosis (TB) vaccine development. Based upon this knowledge we tested other ESX-1 associated proteins as potential TB vaccine antigens.

SUMMARY OF THE INVENTION

The invention is related to preventing and treating infections caused by species of the tuberculosis complex (*M. tuberculosis, M. bovis, M. africanum, M. microti, M. canettii, M. pinnipedii, Mycobacterium mungi*) by the use of a fusion protein or antigen cocktail comprising *M. tuberculosis* antigens selected from ESX-1 associated polypeptides. The fusion proteins or antigen cocktails are used in vaccines preferably together with an adjuvant and/or an immunemodulator.

DETAILED DISCLOSURE OF THE INVENTION

The invention discloses a fusion protein or antigen cocktail, which comprises the amino acid sequences selected from:
a) H74=SEQ ID NO.1 (Rv3881), SEQ ID NO 2 (ESAT-6), SEQ ID NO 3 (Rv3614c), SEQ ID NO 4 (Rv3615c), SEQ ID NO 5 (Rv3616c) and SEQ ID NO 6 (Rv3849), or
b) H164=SEQ ID NO. 2 (ESAT6), SEQ ID NO. 3 (Rv3614c), SEQ ID NO. 6 (Rv3849) and SEQ ID NO. 8 (Rv3872), or
c) H78=SEQ ID NO. 2 (ESAT6), SEQ ID NO. 3 (Rv3614c), SEQ ID NO. 15 (part of Rv3615), SEQ ID NO. 6 (Rv3849) and SEQ ID NO. 8 (Rv3872), or
d) H174=SEQ ID NO.1 (Rv3881), SEQ ID NO 2 (ESAT-6), SEQ ID NO 3 (Rv3614c), SEQ ID NO 5 (Rv3616c) and SEQ ID NO 6 (Rv3849), or
e) H264=SEQ ID NO. 2 (ESAT6), SEQ ID NO. 6 (Rv3849) and SEQ ID NO. 8 (Rv3872), or
f) H274=SEQ ID NO.1 (Rv3881), SEQ ID NO 2 (ESAT-6), SEQ ID NO 5 (Rv3616c) and SEQ ID NO 6 (Rv3849), or
g) H374=SEQ ID NO.1 (Rv3881), SEQ ID NO 2 (ESAT-6) and SEQ ID NO 6 (Rv3849), or
an amino acid sequence analogue having at least 80% sequence identity hereto and at the same time being immunogenic.

The cysteines in the fusion protein according to the invention have preferably been replaced by another amino acid to avoid sulhur-bridge formation and protein aggregation. A preferred replacement amino acid is serine.

The fusion partners of the fusion protein according to the invention is preferably linked with a linker molecule to allow for protein folding and dimer formation.

A preferred embodiment is the fusion protein comprising SEQ ID NO 7 (H74), SEQ ID NO.9 (H164), SEQ ID NO 10 (H174), SEQ ID NO 11 (H264), SEQ ID NO 12 (H274), SEQ ID NO 13 (H374) or SEQ ID NO 14 (H78).

Another embodiment of the invention is using an antigen cocktail according to the invention e.g. the above mentioned amino acid sequences SEQ ID NOS. 1-6, SEQ ID NOS 2, 3, 6 and 8, SEQ ID NOS. 2, 3, 15, 6 and 8, SEQ ID NOS. 1, 2, 3, 5 and 6, SEQ ID NOS 2, 6 and 8, SEQ ID NOS 1, 2 5 and 6 or SEQ ID NOS 1, 2 and 6 without fusing the polypeptides together.

In a still further embodiment, the invention discloses an immunogenic composition comprising a fusion protein or antigen cocktail as defined above, preferably in the form of a vaccine.

In another embodiment, the invention discloses a method for immunising an animal, including a human being, against tuberculosis caused by virulent mycobacteria, e.g. by *Mycobacterium tuberculosis, Mycobacterium africanum, Mycobacterium bovis M. microti, M. canettii, M. pinnipedii* or *Mycobacterium mungi*, comprising administering to the animal the polypeptide as defined above, the immunogenic composition according to the invention, or the vaccine according to the invention.

The vaccine, immunogenic composition and pharmaceutical composition according to the invention can be used prophylactically in a subject not infected with a virulent *mycobacterium* or therapeutically in a subject already infected with a virulent *mycobacterium*.

Definitions

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a purification tag (e.g. his-tag) or a signal peptide. Purification tag's are used to obtain highly pure protein preparations and for e.g the His-tag comprises a methionine as the first animo acid followed by 6-8 histidines if used N-terminal, and 6-8 histidines followed by a STOP-codon if used C-terminal. When used N-terminal the methionine start codon in the gene coding for the polypeptide fusion can be deleted to avoid false translational start sites. The same is true if the gene contains one of the alternative start codons GUG or UUG which normally codes for valine and leucine, respectively, but, as a start codon, they are translated as methionine or formylmethionine.

Each polypeptide is encoded by a specific nucleic acid sequence. It will be understood that such sequences include analogues and variants hereof wherein such nucleic acid sequences have been modified by substitution, insertion, addition or deletion of one or more nucleic acid. Substitutions are preferably silent substitutions in the codon usage which will not lead to any change in the amino acid sequence, but may be introduced to enhance the expression of the protein.

Secretion Systems

Type VII secretion system (T7SS) is a recent discovery in bacterial secretion systems that was first identified in *Mycobacterium tuberculosis*. The corresponding gene clusters were referred to as the ESX (ESAT-6 Secretion System) regions[4-6]. The genome of *M. tuberculosis* H37Rv contains five gene clusters that have evolved through gene duplication events and include components of the T7SS secretion machinery. These clusters are called ESAT-6 secretion system (ESX) 1 through 5. The ESX systems have been shown to secrete proteins lacking classical signal peptides. Furthermore, most of the proteins secreted by ESX1-5 follow a pairwise dependency for secretion[7].

Esx-Family

Except for Rv3017c (esxR) the genes encoding the ESAT-6 family proteins are arranged in tandem pairs at 11 loci on the *M. tuberculosis* H37Rv chromosome and are often preceded by a pe-ppe gene pair. They encode proteins that are approximately 100 amino acids in length and are secreted by the ESX1-5 systems Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

An immunogenic polypeptide is defined as a polypeptide that induces an immune response in a biological sample or an individual currently or previously infected with a virulent *mycobacterium*.

The immune response may be monitored by one of the following methods:

An in vitro cellular response is determined by release of a relevant cytokine such as IFN-γ, from lymphocytes withdrawn from an animal or human being currently or previously infected with virulent mycobacteria, or by detection of proliferation of these T cells. The induction being performed by the addition of the polypeptide or the immunogenic portion to a suspension comprising from $1\times10^5$ cells to $3\times10^5$ cells per well. The cells being isolated from either the blood, the spleen, the liver or the lung and the addition of the polypeptide or the immunogenic portion resulting in a concentration of not more than 20 μg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFN-γ) is the ELISPOT method where the cells isolated from either the blood, the spleen, the liver or the lung are diluted to a concentration of preferable of 1 to $4\times10^6$ cells/ml and incubated for 18-22 hrs in the presence of of the polypeptide or the immunogenic portion resulting in a concentration of not more than 20 μg per ml. The cell suspensions are hereafter diluted to 1 to $2\times10^6$/ml and transferred to Maxisorp plates coated with anti-IFN-γ and incubated for preferably 4 to 16 hours. The IFN-γ producing cells are determined by the use of labelled secondary anti-IFN-γ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an *M. tuberculosis* infected person where the T cell lines have been driven with either live mycobacteria, extracts from the bacterial cell or culture filtrate for 10 to 20 days with the addition of IL-2. The induction being performed by addition of not more than 20 μg polypeptide per ml suspension to the T cell lines containing from $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo cellular response which may be determined as a positive DTH response after intradermal injection or local application patch of at most 100 µg of the polypeptide or the immunogenic portion to an individual who is clinically or subclinically infected with a virulent Mycobacterium, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent Mycobacterium. Readout for induced protection could be decrease of the bacterial load in target organs compared to non-vaccinated animals, prolonged survival times compared to non-vaccinated animals and diminished weight loss compared to non-vaccinated animals.

Immunogenic Portion

In a preferred embodiment of the invention, the polypeptide comprises an immunogenic portion of the polypeptide, such as an epitope for a B-cell or T-cell. The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999).

In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-γ assay described herein. Another method utilises overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind (Stryhn et al. 1996) and hereafter produce these peptides synthetic and test them in relevant biological assays e.g. the IFN-γ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al 1998.

Although the minimum length of a T-cell epitope has been shown to be at least 6 amino acids, it is normal that such epitopes are constituted of longer stretches of amino acids.

Immunogenic portions of polypeptides may be recognised by a broad part (high frequency) or by a minor part (low frequency) of the genetically heterogenic human population. In addition some immunogenic portions induce high immunological responses (dominant), whereas others induce lower, but still significant, responses (subdominant). High frequency><low frequency can be related to the immunogenic portion binding to widely distributed MHC molecules (HLA type) or even by multiple MHC molecules (Kilgus et al. 1991, Sinigaglia et al 1988).

In the context of providing candidate molecules for a new vaccine against tuberculosis, the subdominat epitopes are however as relevant as are the dominat epitopes since it has been show (WO2008000261) that such epitopes can induce protection regardless of being subdominant.

A common feature of the polypeptides of the invention is their capability to induce an immunological response as illustrated in the examples. It is understood that a variant of a polypeptide of the invention produced by substitution, insertion, addition or deletion is also immunogenic determined by any of the assays described herein.

Fusion Proteins

By the term "fusion protein" is understood a random order of two or more immunogenic polypeptides from M. tuberculosis or analogues thereof fused together with or without an amino acid linker/spacer(s) of arbitrary length and sequence. To avoid protein aggregation in the down-stream production all cysteines in the fusion protein can be replaced with any amino acid but serine is the preferred substitute because of its high structural similarity with cysteine Linkers Linkers or spacers are short peptide sequences that occur between polypeptide partners in a fusion protein. Linkers are often composed of flexible residues like glycine and serine so that the adjacent protein domains are free to move relative to one another and for independent proper folding during secretion/manufacturing. Longer linkers are used when it is necessary to ensure that two adjacent domains do not sterically interfere with one another.

Paralogue, Ortologue and Homologue

By the term "paralogue" is understood proteins or genes that share some degree of homology because of shared ancestry followed by one or more duplication event(s). Paralogues are genes related by duplication within a genome while orthologs, which are homologous genes in different species that evolved from a common ancestral gene by speciation, The term, homologue apply to the relationship between genes separated by the event of speciation (ortholog) or to the relationship between genes separated by the event of genetic duplication (paralog).

Analogue

By the term sequence analogue is meant polypeptides which are structurally and immunogenically similar to each other but differs in amino acid composition Vaccine Another part of the invention pertains to a vaccine composition comprising a fusion protein according to the invention. An effective vaccine, wherein a fusion protein the invention is recognized by the animal, will in an animal model be able to decrease bacterial load in target organs, prolong survival times and/or diminish weight loss after challenge with a virulent *Mycobacterium*, compared to non-vaccinated animals In order to ensure optimum performance of such a vaccine composition it is preferred that it comprises an immunologically and pharmaceutically acceptable carrier, vehicle or adjuvant.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of cationic liposomes (e.g. dimethyldioctadecylammonium bromide (DDA)), Quil A, poly I:C, aluminium hydroxide, Freund's incomplete adjuvant, IFN-γ, IL-2, IL-12, monophosphoryl lipid A (MPL), Trehalose Dimycolate (TDM), Trehalose Dibehenate (TDB), Muramyl Dipeptide (MDP) and monomycolyl glycerol (MMG) or combinations hereof.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an antigen of the present invention can be conjugated to an antibody (or antigen binding antibody fragment) against the FCγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 µg to 1000 µg, such as in the range from about 1 µg to 300 µg, and especially in the range from about 10 µg to 50 µg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with virulent mycobacteria and/or to treat established mycobacterial infection. When administered to prevent an infection, the vaccine is given prophylactically, before definitive clinical signs or symptoms of an infection are present.

The invention also pertains to a method for immunising an animal, including a human being, against TB caused by virulent mycobacteria, comprising administering to the animal the polypeptide of the invention, or a vaccine composition of the invention as described above, or a living vaccine described above.

Therapeutic Vaccine.

The invention also relates to the use of a fusion protein of the invention for use as therapeutic vaccines based on their ability to diminish the severity of *M. tuberculosis* infection in experimental animals or prevent reactivation of previous infection, when administered as a vaccine. The composition used for therapeutic vaccines can be prepared as described above for vaccines.

Fusion Proteins Comprising ESX-1 Associated Polypeptides

Mycobacteria secretion systems are responsible for the export of virulence factors either to extracellular environment or directly into the host cell and thus, play a vital role in the virulence and survival of the bacteria. Part of the ESX-1 secretion system was identified during the comparative genomic analysis of attenuated *M. bovis* BCG and pathogenic mycobacterial species[8]. One of the main genome differences was a major deletion in the *M. bovis* genome that included the region encoding the secreted antigens CFP10 and ESAT-6. This region was observed to be especially responsible for virulence and restoration of the region not only enabled the secretion of ESAT-6, but also led to increased virulence in *M. bovis* BCG[4].

The ESX-1 secretion system is conserved among slow growing mycobacteria including all pathogenic mycobacteria within the *M. tuberculosis* complex and is required for survival of mycobacteria in vivo. The functions of the secreted effector molecules are required for initiation of granuloma formation and phagosome maturation, essential for escape from phagosomes, cell lysis and cell-to-cell spreading, apoptosis through caspase activation and immune modulation by interfering with TLR2 signaling[6,9].

Today we know that the ESX-1 secretion system is encoded by three different loci, the ESX-1 locus, the espA operon and the locus for the transcriptional regulator EspR[10,11].

The exact number of components that are involved in ESX-1 secretion is still debated and seems to vary between different mycobacterial species. Currently the following Mycobacterium tuberculosis genes have shown relation to the ESX-1 system: espR, espA; espB; espC, espD, espF esxA; esxB; mycP1; PE35; Rv3862 (VVhiB6), Rv3866, Rv3868; Rv3869; Rv3870; Rv3871; Rv3876; Rv3877; Rv3879c; Rv3881c Rv3882c and the MCE1 proteins Mce1B, Mce1C MCe1F and Rv0177[12,13].

The six experimentally verified ESX-1 substrates, Rv3616c (EspA), Rv3615c (EspC), Rv3849 (EspR), ESAT-6, CFP-10 and Rv3881c (EspB) are mutually dependent on each other for secretion[7].

All known ESX-1 secreted substrates are strong antigens that are highly expressed in different stages of infection—in contrast to eg. Ag85 and other metabolic related antigens that are downregulated shortly after infection.

Given the high expression at various time point during infection and the high immunogenicity of many ESX-1 associated proteins we made the H74 backbone fusion protein based on six of the ESX-1 associated.

The H74 fusion protein consist of three experimentally proven ESX-1 substrates (ESAT-6, EspR, EspC) plus three secreted proteins associated with ESX-1 (EspD, EspA, EspB). The order of proteins in the H74 fusion is: EspB, ESAT-6, Rv3614, EspC, EspA, EspR. H74 consists of 1319 amino acids, the theoretical molecular weight is 137,917 g/mol and the isoelectric point 4.77. In the wild type sequence encoded from the *Mycobacterium tuberculosis* chromosome there is one cysteine in EspD, EspC and EspR. To avoid problems with sulphur-bridge formation and protein aggregation during refolding all three cysteines have been replaced with the amino acid serine.

Info on the individual proteins in H74:

ESAT-6 (Rv3875) is, together with CFP10, secreted via ESX-1 as a heterologous dimer[14].

EspR (Rv3849) is a transcriptional activator of its own expression and an operon that includes espA (Rv3616c), C and D. The EspR protein is secreted via ESX-1[15].

EspC (Rv3615c) gene expression is regulated by EspR. EspC is secreted by ESX-1[11].

EspD (Rv3614c) gene expression is regulated by EspR. EspD is co-transcribed with espC and espA. EspD expression but not secretion is required for EsxA secretion. EspD stabilizes the EspA-EspC complex. EspD secretion does not exclusively require the ESX-1 system[16].

EspA (Rv3616) gene expression is regulated by EspR. EspA is secreted by ESX-1[7].

EspB (Rv3881) is secreted by ESX-1 {Xu, 2007 #912; McLaughlin, 2007 #591}.

Info on the individual proteins in H78:

ESAT-6 (Rv3875) is, together with CFP10, secreted via ESX-1 as a heterologous dimer[14].

EspD (Rv3614c) gene expression is regulated by EspR. EspD is co-transcribed with espC and espA. EspD expression but not secretion is required for EsxA secretion. EspD stabilizes the EspA-EspC complex. EspD secretion does not exclusively require the ESX-1 system[16].

Amino acid 1-56 of the EspC (Rv3615c) protein sequence. The espC gene expression is regulated by EspR. EspC protein is secreted by ESX-1[11].

EspR (Rv3849) is a transcriptional activator of its own expression and an operon that includes espA (Rv3616c), C and D. The EspR protein is secreted via ESX-1[15].

PE35 (Rv3872) is a secreted PE protein. Inactivation of gene pe35 (Rv3872) impaired expression of CFP-10 and ESAT-6, suggesting a role in regulation.

FIGURE LEGENDS

FIG. 1. Antigen Specific Immune Responses after Vaccination.

After vaccination of animals with either the fusion proteins H74 or H56 formulated in CAF01 adjuvant the strength and specificity of T cell responses were measured. Responses towards the combined six proteins in H74 or three proteins in H56 was quantitated in PBMC's isolated from blood (A and C) or in spelocytes (B and D) by stimulating the cells with either 2 ug H74 or H56 antigen pools The antigen specificity was measured by restimulaing with 2 ug of each of the single antigens in the two vaccines (E and F).

Readout was secreted IFN-γ that was measured in culture supernatants by ELISA after three days of in vitro stimulation.

FIG. 2. Vaccine Induced T Cell Polyfunctionality and Protective Efficacy.

Using flow cytometry the frequency of vaccine specific CD4 T cells capable of producing at least one of the cytokines IFN-γ, TNF-α or IL-2 was measured after stimulation with vaccine antigens (A). PBS stimulation controls were substtracted. The cytokine expression profile of the three cytokines was measured for individual CD4 T cells and the frequency of tridple, double and single cytokine producing T cells tabulated for four individual animals per group. In total there is seven combinations of the three cytokines The pie charts illustrate the distribution of cytokine producing subtypes for each vaccination group (B). The same color coding is used for all six pie's. After being aerosolly challenged with *Mycobacterium tuberculosis* the bacterial burden in the lung of individual animals was measured and compared among the groups (C). Statistical comparison of the groups was done by one-way-ANOVA and Tukey's multiple comparison post test (*$p<0.001$; $p<0.01$; *$p<0.05$). The mean and SEM are shown for each group.

FIG. 3. A Broad Range of H74 Vaccine Doses can Improve BCG Protection.

(A) The number of Mycobacterial tuberculosis bacteria was determined in groups of mice after twelve weeks infection with *M.tb* strain Erdman. The animals were vaccinated with either BCG alone or BCG followed by H74 formulated in CAF01 adjuvant three months later. To identify a relevant H74 vaccine dose five different doses of H74 were tested (from 0.01 ug to 25 ug). Based upon one way analysis of variance (ANOVA) and Tukey's multiple comparisons test showed that all vaccinated groups had significant lower CFU numbers relative to the saline control (black circles, $p<0.001$). Even though the 0.1; 1 and 5 ug H74 vaccination groups had lower CFU's than the BCG only vaccinated group (red circles) the difference was not significant. (B) Repeat of the experiment using 0.1 or 5 ug H74 showed that H74 significantly reduced the CFU load in protected animals with a prior BCG vaccination (*, $p<0.05$ compared to the BCG only vaccinated groups).

Figure 4:
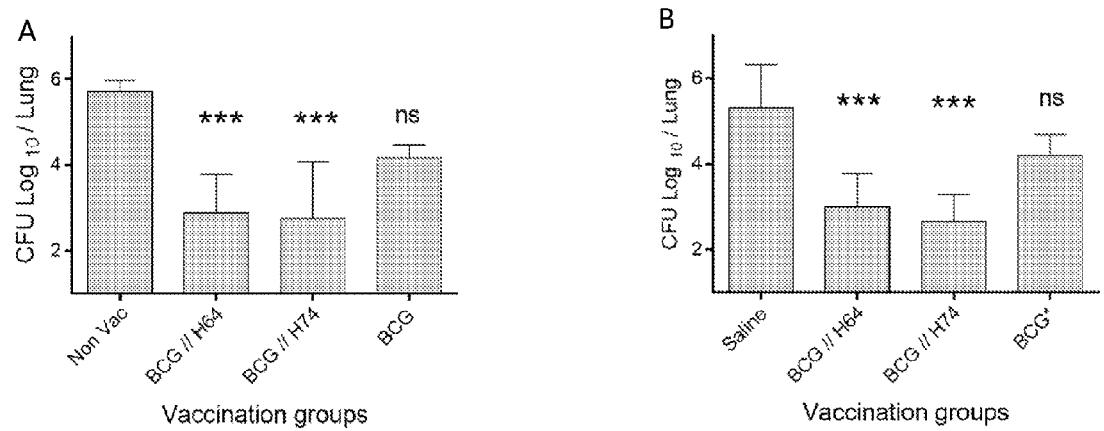

FIG. 4. H64 and H74 can Supplement the BCG Vaccine and Induce Long-Term Protection against Clinical Isolates of Mtb.

The number of Mycobacterial tuberculosis bacteria was determined in groups of mice after twenty-four weeks infection with either M.tb strain Beijing (A) or Kazakhstan (B). In both experiments animals were vaccinated with either BCG alone or BCG followed by either 2 ug of H64 or H74 formulated in CAF01 adjuvant two months later. Only in animals from vaccination groups where BCG was supplemented with either H64 or H74 was the reduction in bacteria load statistical significant (p<0.05) based upon one way analysis of variance (ANOVA) and Tukey's multiple comparisons test.

Figure 5:
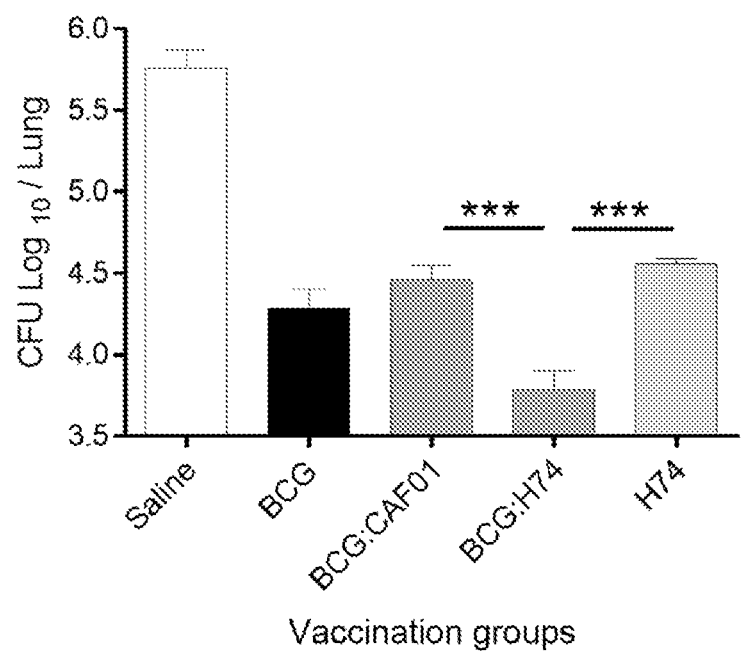

FIG. 5. H74 Protects Against M.tb Challenge and can Supplement BCG for Improved Protection when Injected at the same time as BCG.

Groups of mice were either vaccinated once with BCG, three times with H74/CAF01 or once with BCG and H74/CAF01 (injected at two different sites) followed by two H74/CAF01 vaccinations. After six weeks infection with Mtb strain Erdman the bacterial load was determined. All vaccines gave significant protection (p<0.001) but the injection of both BCG and H74 in the first vaccination round induced significantly better protection than either of the vaccines on their own (p<0.001).

Figure 6:
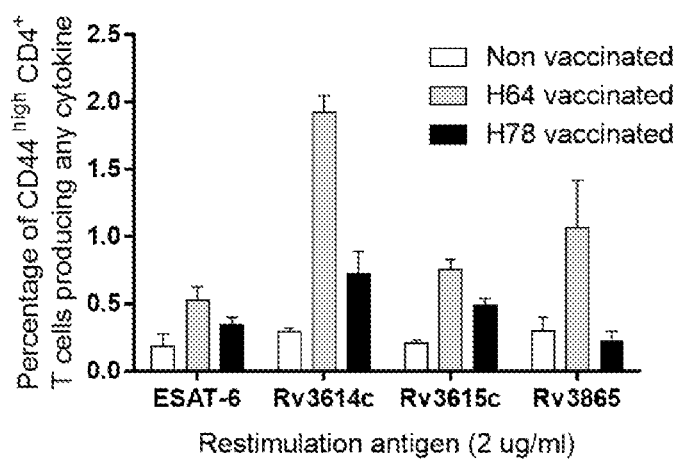

FIG. 6. T Cell Responses after H64 or H78 Vaccination.

Spleen cells from H64 or H78 vaccinated mice were isolated from individual animals and stimulated with 2 ug/ml of either ESAT-6, Rv3614c, Rv3615c or Rv3865 at 37° C. for 6 hours. After washing the cells were stained with fluorescent labelled antibodies against the surface markers CD4 and CD44 and the cytokines IFN-g, TNF-a, IL-2 and IL17. The expression of the labelled markers and cytokines was measured by flowcytometri. After gating for high expression of CD4 and CD44 the frequency of cytokine producing cells in this subgroup of activated T cells was plotted.

EXAMPLES

Example 1

The H74 Fusion Protein-Immune Responses and Protection in a Preventive TB Vaccination Model.

Figure 2:
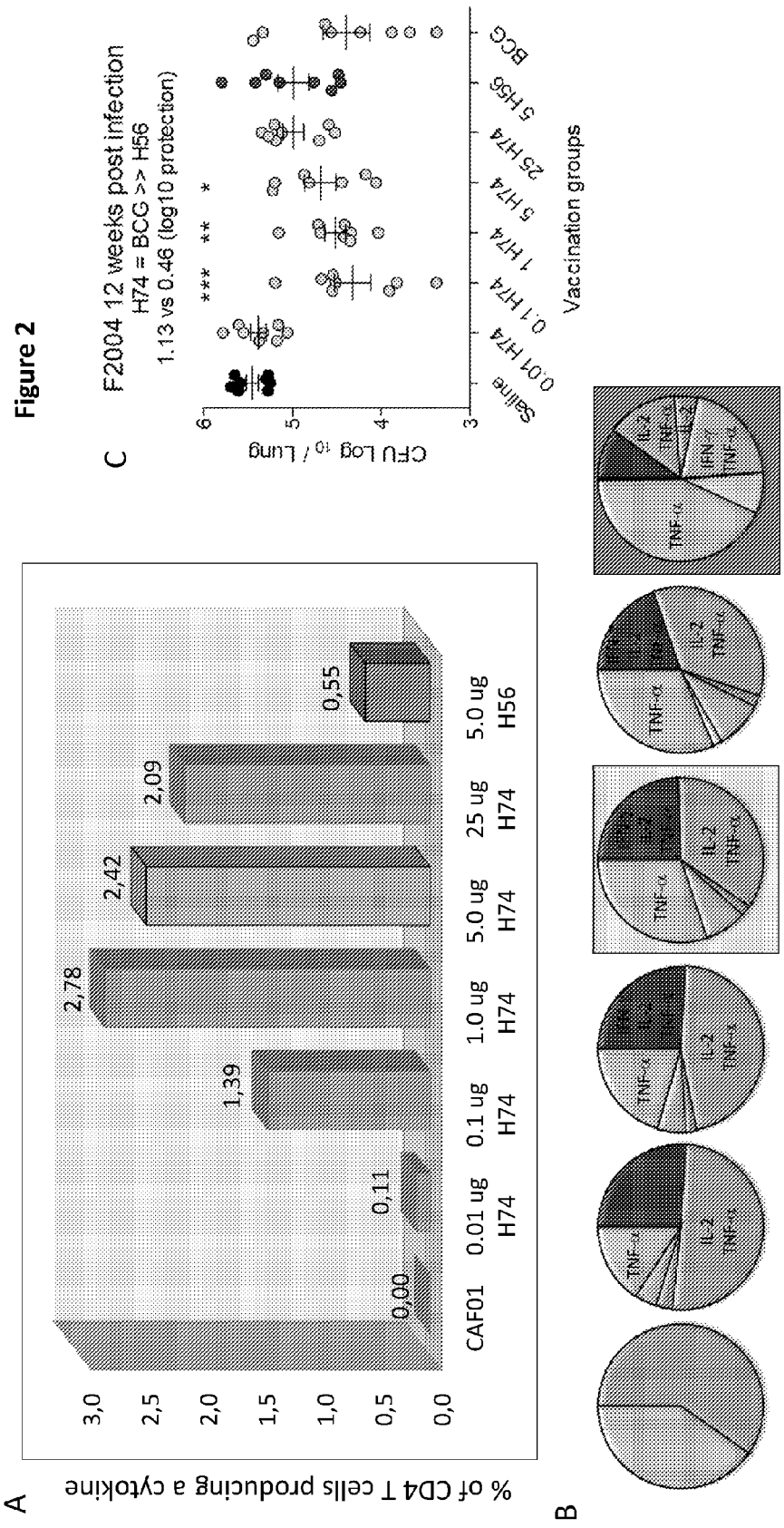

Groups of CB6F1 mice were vaccinated three times with either 0.01; 0.1, 1, 5 or 25 ug of the fusion protein H74 or 5 ug of the fusion protein H56. Both proteins were formulated in the liposome based adjuvant CAF01 prior to injection. Control groups were injected 3 times with an equal volume of saltwater (200 uL) or vaccinated once with 200 uL BCG ($5 \times 10^7$ CFU/mL). Spacing between vaccination were 2 weeks and. Three weeks after $3^{rd}$ vaccination PBMC's and splenocytes were isolated and the vaccine induced T cell responses were measured. Isolated cells ($5 \times 10^6$/well) were incubated with 2 ug of the individual proteins present in the two fusion proteins or 2 ug of the fusion proteins for three days and sected IFN-g measured in the media by ELISA (FIG. 1A-F). In the H56 vaccinated control animals there is strong recognition of the H56 protein and Ag85B and a moderate ESAT-6 recognition. H74 vaccinated animals have a strong response specific for Rv3881c and a moderate reposnse against Rv3849c and Rv3616c. In this inbred mice strain there is no response towards Rv3615c or Rv3614c. There is no response in the saline injected animals confirming the responses are vaccine specific. The strength of the H74 response was strongest in the animals receiving either 1 or 5 ug of the H74 protein depending upon the organ (FIGS. 1A and B). However, even the low 0.1 ug dose of H74 gave higher IFN-γ release than vaccinating with 5 ug of H56 protein. Looking at additional cytokines produced by spleen T cells the maximum frequency of responding T cells was found in the 1 ug H74 group but again 0.01 ug H74 gave higher response than 5 ug of H56 (FIG. 2A). In therms of vaccine dose and polyfunctionality of the T cells there was an inverse correlation between the relative fraction of IL-2 producing T cells and H74 vaccination dose (FIG. 2B).

Six weeks after third vaccination all animals were aerosolly challenge with virulent M. tuberculosis strain Erdman. Twelve weeks after challenge all mice were euthanized and the number of bacteria in lungs of individual animals was determined by plating dilutions of lung homogenate and counting the number of colonies (FIG. 2C). Three of the H74 vacine doses and BCG all induced significant protection compared to the saline control group. Importantly the control vaccine, H56, vaccine did not induce a statistically level of protection at this timepoint.

Example 2

The H74 and H64 Fusion Proteins as a Supplement Vaccine to BCG. Except for Control Animals, all CB6F1 Mice were BCG Vaccinated.

Figure 3:
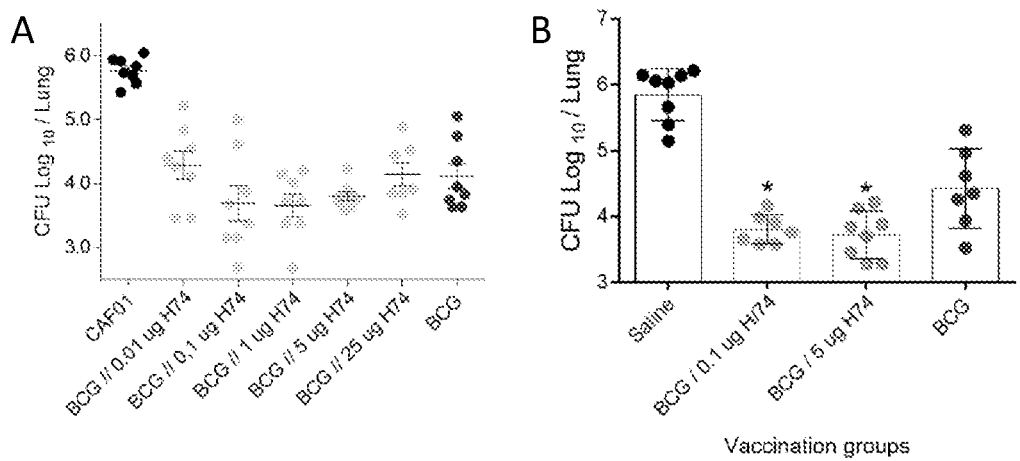

To determine the optimal H74 dose for vaccination on top of a BCG vaccine groups of BCG vaccinated animals where vaccinated three times with different doses of the fusion proteins H74 formulated in the liposome based adjuvant CAF01. The first H74 vaccination was injected three month after the BCG vaccination. Control animals received four injections with volume of saltwater (no BCG, no H74) or where vaccinated once with BCG. Spacing between the H74 vaccinations were 2 weeks. Six weeks after the 3rd H74 vaccination animals were aerosolly challenge with virulent M. tuberculosis Erdman. Twelve weeks later all mice were euthanized and the number of bacteria in lungs of individual animals was determined by plating dilutions of lung homogenate and counting the number of colonies (FIGS. 3A and B).

H74 doses from 0.1 ug to 5 ug induces a similar level of protection with CFU numbers slightly lower than in the BCG only vaccinated animals. All vaccinated groups induced significant protection compared to the saline control (p<0.001). In a repeat experiment (FIG. 3B) only including the H74 vaccination doses 0.1 ug and 5 ug H74 the results were similar. All vaccinated animals had significantly lower bacteria load (p<0.001) but this time the H74 supplement groups also had significantly lower CFU's that the BCG only vaccinated group. To compare the H74 and H64 as BCG supplement vaccines animals were BCG vaccinated and two months later vaccinated with either 0.1 ug H64/CAF01 or H74/CAF01 as above. In this experiment the animals were challenge with either the clinical Mtb isolate Beijing (FIG. 4A) or clinical M.tb isolate Kazakhstan (FIG. 4B) six weeks after the third H64 or H74 vaccination. After twenty-four weeks infection the bacterial load was enumerated in individual lungs. At this late time point, the protective efficacy of BCG against any of the isolates was not significant. However, supplementing BCG with either H64 or H74 gave significant protection against both clinical isolates of M.tb (p<0.001).

Example 3

H74 can Supplement BCG Even if the First Vaccination is at the Same Time Point as BCG Vaccination.

There is four vaccination groups and one saline control group in this experiment. One vaccination group received only BCG and one group received three times 5 ug H74/CAF01. The remaining two groups received a BCG vaccination with one syringe and either a H74/CAF01 or CAF01 vaccination with another syringe (side-by-side vaccination) as their first vaccination. In the second and third vaccination, they received H74/CAF01 or CAF01 respectively. Six weeks after third vaccination all animals were challenge with Mtb strain Erdman and six weeks later the CFU numbers were determined in lungs as above (FIG. 5). All vaccines induces significant protection (p<0.001) and the level for the BCG, BCG:CAF01 and H74 were similar. However, the animals in the group receiving BCG:H74 and two times H74 boost had significantly lower bacteria in the lungs than the other vaccinations groups—BCG, BCG:CAF01 and H74 (p<0.001).

Example 4

H78 and H64 Vaccination Induces Comparable T Cells Responses Against the Major Antigens in the Fusion Proteins.

The H64 fusion protein is comprised of six proteins from *Mycobacterium tuberculosis*. Two of these, Rv3865 and Rv3615, are recognized with high frequency and specificity in TB patients and therefore have important value as protein antigens in coming TB diagnostic kits. Due to the antigen overlap, a worldwide use of a H64 vaccine would compromise the diagnostic kits. To avoid this problem full-length Rv3865 and half of the Rv3615 protein were removed from H64 to create a slightly shorter fusion protein named H78. To compare the ability of H64 and H78 to induce immune responses groups of animals were vaccinated three times with either 2 ug H64 or H78 formulated in CAF01 adjuvant or injected with saline three times. Three weeks after third vaccination three animals from each group were sacrificed and the T cell responses against the most important antigens was measured in spleen cells by flow cytometry (FIG. 6). Both H64 and H78 induces the expected antigen pattern. H64 induced T cell responses against all four antigens investigated (ESAT-6, Rv3615c, Rv3614c and Rv3865). As expected, there was no response against Rv3865 in H78 vaccinated animals but, quite importantly, there was still a specific response against Rv3615c with a T cell frequency similar to that found in H64 vaccinated animals despite H78 is lacking half of the Rv3615c protein.

REFERENCES

1. Cole, S. T., et al. Deciphering the biology of *Mycobacterium tuberculosis* from the complete genome sequence. *Nature* 393, 537-544 (1998).
2. Bold, T. D., Banaei, N., Wolf, A. J. & Ernst, J. D. Suboptimal activation of antigen-specific CD4+ effector cells enables persistence of *M. tuberculosis* in vivo. *PLoS Pathog* 7, e1002063 (2011).
3. Egen, J. G., et al. Intravital imaging reveals limited antigen presentation and T cell effector function in mycobacterial granulomas. *Immunity* 34, 807-819 (2011).
4. Pym, A. S., et al. Recombinant BCG exporting ESAT-6 confers enhanced protection against tuberculosis. *Nat Med* 9, 533-539 (2003).
5. Stanley, S. A., Raghavan, S., Hwang, W. W. & Cox, J. S. Acute infection and macrophage subversion by *Mycobacterium tuberculosis* require a specialized secretion system. *Proc Natl Acad Sci USA* 100, 13001-13006 (2003).
6. Abdallah, A. M., et al. Type VII secretion—mycobacteria show the way. *Nat Rev Microbiol* 5, 883-891 (2007).
7. Fortune, S. M., et al. Mutually dependent secretion of proteins required for mycobacterial virulence. *Proc Natl Acad Sci USA* 102, 10676-10681 (2005).
8. Gordon, S. V., et al. Identification of variable regions in the genomes of tubercle bacilli using bacterial artificial chromosome arrays. *Mol Microbiol* 32, 643-655 (1999).
9. Gao, L. Y., et al. A mycobacterial virulence gene cluster extending RD1 is required for cytolysis, bacterial spreading and ESAT-6 secretion. *Mol Microbiol* 53, 1677-1693 (2004).
10. MacGurn, J. A. & Cox, J. S. A genetic screen for *Mycobacterium tuberculosis* mutants defective for phagosome maturation arrest identifies components of the ESX-1 secretion system. *Infect Immun* 75, 2668-2678 (2007).
11. MacGurn, J. A., Raghavan, S., Stanley, S. A. & Cox, J. S. A non-RD1 gene cluster is required for Snm secretion in *Mycobacterium tuberculosis*. *Mol Microbiol* 57, 1653-1663 (2005).
12. Bahk, Y. Y., et al. Antigens secreted from *Mycobacterium tuberculosis*: identification by proteomics approach and test for diagnostic marker. *Proteomics* 4, 3299-3307 (2004).
13. Das, C., Ghosh, T. S. & Mande, S. S. Computational analysis of the ESX-1 region of *Mycobacterium tuberculosis*: insights into the mechanism of type VII secretion system. *PLoS ONE* 6, e27980 (2011).
14. Champion, P. A., Stanley, S. A., Champion, M. M., Brown, E. J. & Cox, J. S. C-terminal signal sequence promotes virulence factor secretion in *Mycobacterium tuberculosis*. *Science* 313, 1632-1636 (2006).
15. Raghavan, S., Manzanillo, P., Chan, K., Dovey, C. & Cox, J. S. Secreted transcription factor controls *Mycobacterium tuberculosis* virulence. *Nature* 454, 717-721 (2008).
16. Chen, J. M., et al. EspD is critical for the virulence-mediating ESX-1 secretion system in *Mycobacterium tuberculosis*. *J Bacteriol* 194, 884-893 (2012).
17. Brodin, P., et al. Dissection of ESAT-6 system 1 of *Mycobacterium tuberculosis* and impact on immunogenicity and virulence. *Infect Immun* 74, 88-98 (2006).
18. Ohol, Y. M., et al. *Mycobacterium tuberculosis* MycP1 protease plays a dual role in regulation of ESX-1 secretion and virulence. *Cell Host Microbe* 7, 210-220 (2010).

The invention claimed is:

1. A fusion protein, which comprises the amino acid sequences selected from:
 a) SEQ ID NO: 1 (Rv3881), SEQ ID NO: 2 (ESAT-6), SEQ ID NO: 3 (Rv3614c), SEQ ID NO: 4 (Rv3615c), SEQ ID NO: 5 (Rv3616c) and SEQ ID NO: 6 (Rv3849),
 b) SEQ ID NO: 2 (ESAT6), SEQ ID NO: 3 (Rv3614c), SEQ ID NO: 6 (Rv3849) and SEQ ID NO: 8 (Rv3872),
 c) SEQ ID NO: 2 (ESAT6), SEQ ID NO: 3 (Rv3614c), SEQ ID NO: 15, SEQ ID NO: 6 (Rv3849) and SEQ ID NO: 8 (Rv3872),
 d) SEQ ID NO: 1 (Rv3881), SEQ ID NO: 2 (ESAT-6), SEQ ID NO: 3 (Rv3614c), SEQ ID NO: 5 (Rv3616c) and SEQ ID NO: 6 (Rv3849),
 e) SEQ ID NO: 2 (ESAT6), SEQ ID NO: 6 (Rv3849) and SEQ ID NO: 8 (Rv3872), f) SEQ ID NO: 1 (Rv3881), SEQ ID NO: 2 (ESAT-6), SEQ ID NO: 5 (Rv3616c) and SEQ ID NO: 6 (Rv3849), g) SEQ ID NO: 1 (Rv3881), SEQ ID NO: 2 (ESAT-6) and SEQ ID NO: 6 (Rv3849), and an amino acid sequence having at least 90% sequence identity to any one of (a)-(g) over the full sequences recited in any one of (a)-(g) and at the same time being immunogenic.

2. The fusion protein according to claim 1 wherein the cysteines have been replaced by another amino acid to avoid sulphur-bridge formation and protein aggregation.

3. The fusion protein according to claim 2, wherein the cysteines have been replaced with serine.

4. The fusion protein according to claim 1, wherein the amino acid sequences are linked with a linker molecule.

5. The fusion protein according to claim 4 with the amino acid sequence SEQ ID NO: 7 (H74), SEQ ID NO: 9 (H164), SEQ ID NO: 10 (H174), SEQ ID NO: 11 (H264), SEQ ID NO: 12 (H274), SEQ ID NO: 13 (H374) or SEQ ID NO: 14 (H78).

6. A vaccine comprising a fusion protein according to claim 1.

7. The vaccine according to claim 6 additionally comprising an adjuvant.

8. The vaccine according to claim 7 where the adjuvant is selected from the group consisting of cationic liposomes, Quil A, poly I:C, aluminium hydroxide, Freund's incomplete adjuvant, IFN-γ, IL-2, IL-12, monophosphoryl lipid A (MPL), Trehalose Dimycolate (TDM), Trehalose Dibehenate (TDB), Muramyl Dipeptide (MDP) and monomycolyl glycerol (MMG) or combinations hereof.

9. A method for immunizing an animal against tuberculosis caused by virulent mycobacteria, comprising administering to the animal a vaccine according to claim 6.

10. The method according to claim 9, wherein said animal is a human being.

11. The method according to claim 9, wherein said virulent mycobacteria is selected from the group consisting of *Mycobacterium tuberculosis, Mycobacterium africanum*, and *Mycobacterium bovis*.

12. The fusion protein according to claim 1, wherein the amino acid sequence having at least 90% sequence identity to any one of (a)-(g) over the full sequences recited in any one of (a)-(g) has at least 95% sequence identity to said sequences.

13. The vaccine according to claim 8, wherein said cationic liposomes comprise dimethyldioctadecylammonium bromide (DDA).

14. A fusion protein comprising the amino acid sequences SEQ ID NO: 1 (Rv3881), SEQ ID NO: 2 (ESAT-6), SEQ ID NO: 3 (Rv3614c), SEQ ID NO: 4 (Rv3615c), SEQ ID NO: 5 (Rv3616c) and SEQ ID NO: 6 (Rv3849), or an amino acid sequence having at least 90% sequence identity to SEQ ID NOS: 1, 2, 3, 4, 5, and 6 over their full sequences and at the same time being immunogenic.

15. The fusion protein according to claim 14, wherein the amino acid sequence having at least 90% identity to SEQ ID NOS: 1, 2, 3, 4, 5, and 6 over their full sequences has at least 95% sequence identity to said sequences.

16. The fusion protein according to claim 15, wherein said fusion protein is SEQ ID NO: 7 (H74).

17. The fusion protein according to claim 14 wherein the cysteines have been replaced by another amino acid to avoid sulphur-bridge formation and protein aggregation.

18. The fusion protein according to claim 17, wherein the cysteine have been replaced with serine.

19. The fusion protein according to claim 14, wherein the fusion partners are linked with a linker molecule.

* * * * *